(12) United States Patent
Fischer et al.

(10) Patent No.: US 11,019,821 B2
(45) Date of Patent: Jun. 1, 2021

(54) FUSED BICYCLIC HETEROCYCLE DERIVATIVES AS PESTICIDES

(71) Applicant: Bayer Aktiengesellschaft, Leverkusen (DE)

(72) Inventors: Ruediger Fischer, Pulheim (DE); Dominik Hager, Monheim (DE); Laura Hoffmeister, Duesseldorf (DE); Matthieu Willot, Duesseldorf (DE); Kerstin Ilg, Cologne (DE); Ulrich Goergens, Ratingen (DE); Andreas Turberg, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 16/971,250

(22) PCT Filed: Feb. 14, 2019

(86) PCT No.: PCT/EP2019/053631
§ 371 (c)(1),
(2) Date: Aug. 19, 2020

(87) PCT Pub. No.: WO2019/162174
PCT Pub. Date: Aug. 29, 2019

(65) Prior Publication Data
US 2020/0383334 A1 Dec. 10, 2020

(30) Foreign Application Priority Data
Feb. 21, 2018 (EP) ..................... 18157886

(51) Int. Cl.
*A01N 43/90* (2006.01)
*C07D 471/04* (2006.01)
*C07D 519/00* (2006.01)

(52) U.S. Cl.
CPC ........... *A01N 43/90* (2013.01); *C07D 471/04* (2013.01); *C07D 519/00* (2013.01)

(58) Field of Classification Search
CPC ..... A01N 43/90; C07D 471/04; C07D 519/00
See application file for complete search history.

(56) References Cited

U.S. PATENT DOCUMENTS

| | | | |
|---|---|---|---|
| 10,611,779 B2 * | 4/2020 | Fischer | A01N 43/90 |
| 2017/0073342 A1 | 3/2017 | Fischer et al. | |
| 2018/0002345 A1 | 1/2018 | Fischer et al. | |
| 2018/0016273 A1 | 1/2018 | Fischer et al. | |
| 2018/0116222 A1 | 5/2018 | Fischer et al. | |
| 2018/0303097 A1 | 10/2018 | Wilcke et al. | |
| 2018/0305353 A1 | 10/2018 | Fischer et al. | |
| 2019/0239510 A1 | 8/2019 | Willot et al. | |
| 2019/0241564 A1 | 8/2019 | Fischer et al. | |
| 2019/0248811 A1 | 8/2019 | Fischer et al. | |

FOREIGN PATENT DOCUMENTS

| | | |
|---|---|---|
| EP | 3241830 A1 | 11/2017 |
| EP | 3305786 A2 | 4/2018 |
| WO | 2009076440 A2 | 6/2009 |
| WO | 2010125985 A1 | 11/2010 |
| WO | 2012074135 A1 | 6/2012 |
| WO | 2012086848 A1 | 6/2012 |
| WO | 2013018928 A1 | 2/2013 |
| WO | 2013191113 | 12/2013 |
| WO | 2014142292 A1 | 9/2014 |
| WO | 2014148451 A1 | 9/2014 |
| WO | 2015000715 A1 | 1/2015 |
| WO | 2015002211 A1 | 1/2015 |
| WO | 2015059039 A1 | 4/2015 |
| WO | 2015071180 A1 | 5/2015 |
| WO | 2015121136 A1 | 8/2015 |
| WO | 2015190316 A1 | 12/2015 |
| WO | 2016020286 A1 | 2/2016 |
| WO | 2016091731 A1 | 6/2016 |
| WO | 2016107742 A1 | 7/2016 |
| WO | 2016124557 A1 | 8/2016 |
| WO | 2016124563 A1 | 8/2016 |
| WO | 2016129684 A1 | 8/2016 |
| WO | 2016162318 A1 | 10/2016 |
| WO | 2017001311 A1 | 1/2017 |
| WO | 2017001314 A1 | 1/2017 |
| WO | 2017055185 A1 | 4/2017 |
| WO | 2017061497 A1 | 4/2017 |
| WO | 2017072039 A1 | 5/2017 |
| WO | 2017084879 A1 | 5/2017 |
| WO | 2017089190 A1 | 6/2017 |
| WO | 2017093180 A1 | 6/2017 |
| WO | 2017125340 A1 | 7/2017 |
| WO | 2017133994 A1 | 8/2017 |
| WO | 2017174414 A1 | 10/2017 |
| WO | 2018015289 A1 | 1/2018 |
| WO | 2018050825 A1 | 3/2018 |
| WO | 2018095953 A1 | 5/2018 |

(Continued)

OTHER PUBLICATIONS

International Search Report for Application PCT/EP2019/053631 dated Mar. 27, 2019.

(Continued)

*Primary Examiner* — John Mabry
(74) *Attorney, Agent, or Firm* — McBee Moore & Vanik IP, LLC

(57) ABSTRACT

The invention relates to novel compounds of the formula (I)

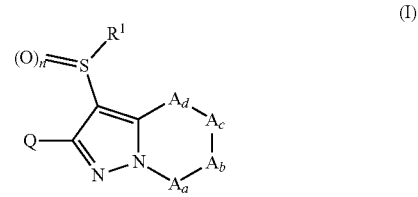

in which Aa, Ab, Ac, Ad, Q, $R^1$ and n have the definitions given above,
to their use as acaricides and/or insecticides for controlling animal pests and to processes and intermediates for their preparation.

11 Claims, No Drawings

(56) References Cited

FOREIGN PATENT DOCUMENTS

WO     2018138050 A1     8/2018
WO     2018141954 A1     8/2018

OTHER PUBLICATIONS

Hiroyuki, Kawai et al., "Regioselective Synthesis of Pyrazole Triflones Based on Triflyl Alkyne Cycloadditions," Organix Letters, (2012), vol. 14, No. 20: 5330-5333.

* cited by examiner

FUSED BICYCLIC HETEROCYCLE DERIVATIVES AS PESTICIDES

CROSS-REFERENCE TO RELATED APPLICATIONS

This application is the National Stage entry of International Application No. PCT/EP2019/053631, filed 14 Feb. 2019, which claims priority to European Patent Application No. 18157886.5, filed 21 Feb. 2018.

BACKGROUND

Field

The present invention relates to novel fused bicyclic heterocycle derivatives of the formula (I), to their use as acaricides and/or insecticides for controlling animal pests, particularly arthropods and especially insects and arachnids, and to processes and intermediates for their preparation.

Description of Related Art

Fused bicyclic heterocycle derivatives having insecticidal properties have already been described in the literature, for example in WO 2010/125985, WO 2012/074135, WO 2012/086848, WO 2013/018928, WO 2013/191113, WO 2014/142292, WO 2014/148451, WO 2015/000715, WO 2016/124563, WO 2016/124557, WO 2016/162318, WO 2017/093180, WO 2017/125340, WO 2017/174414, EP-A 3241830, EP17154789.6, WO 2015/121136, WO 2015/002211, WO 2015/071180, WO 2016/020286, WO 2015/059039, WO 2015/190316, WO 2016/091731, WO 2016/107742, WO 2016/162318, PCT/EP2016/075365, WO 2017/055185, EP3272756, EP 16189445.6, EP 16200177.0, EP17153317.7, WO 2016/129684, WO 2017/001311, WO 2017/001314, WO 2017/061497, WO 2017/084879, WO 2017/089190, WO2017/133994.

Modern crop protection compositions have to meet many demands, for example in relation to extent, persistence and spectrum of their action and possible use. Questions of toxicity, sparing of beneficial species and pollinators, environmental properties, application rates, combinability with other active ingredients or formulation auxiliaries play a role, as does the log P uestion of the complexity involved in the synthesis of an active ingredient, and resistances can also occur, to mention just a few parameters. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which broaden the spectrum of the pesticides in various aspects and/or improve their activity.

Novel fused bicyclic heterocycle derivatives have now been found, these having advantages over the compounds already known, examples of which include better biological or environmental properties, a wider range of application methods, better insecticidal or acaricidal action, and good compatibility with crop plants. The fused bicyclic heterocycle derivatives can be used in combination with further agents for improving efficacy, especially against insects that are difficult to control.

The present invention therefore provides novel compounds of the formula (I)

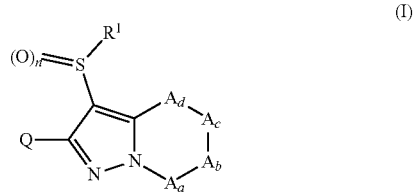

in which (configuration 1-1)
Aa is —$C(R^8)(R^9)$—,
Ab is —$C(R^{10})(R^{11})$—,
Ac is —$C(R^{12})(R^{13})$—,
Ad is —$C(R^{14})(R^{15})$—,
$R^1$ is $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, amino, $(C_1-C_6)$-alkylamino, di-$(C_1-C_6)$-alkyl-amino, $(C_3-C_8)$-cycloalkylamino, $(C_1-C_6)$-alkylcarbonylamino, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-alkyl, $(C_1-C_6)$-haloalkylsulfonyl-$(C_1-C_6)$-alkyl, $(C_1-C_6)$-alkoxy-$(C_1-C_6)$-alkylthio-$(C_1-C_6)$-alkyl, $(C_1-C_6)$-alkoxy-$(C_1-C_6)$-alkylsulfinyl-$(C_1-C_6)$-alkyl, $(C_1-C_6)$-alkoxy-$(C_1-C_6)$-alkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkylsulfonylamino, aminosulfonyl-$(C_1-C_6)$-alkyl, $(C_1-C_6)$-alkylaminosulfonyl-$(C_1-C_6)$-alkyl, di-$(C_1-C_6)$-alkylaminosulfonyl-$(C_1-C_6)$-alkyl,
$R^8$, $R^9$, $R^{10}$, $R^{11}$, $R^{12}$, $R^{13}$, $R^{14}$, $R^{15}$ are independently hydrogen, cyano, halogen, nitro, acetyl, hydroxyl, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, cyano-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$- haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkyl aminothiocarbonyl, $(C_3-C_8)$-cycloalkylamino, NHCO—$(C_1-C_6)$-alkyl ($(C_1-C_6)$-alkylcarbonylamino), are in each case optionally singly or multiply, identically or differently substituted aryl or hetaryl, where (in the case of hetaryl) at least one carbonyl group may optionally be present and/or where possible substituents in each case are as follows: cyano, carboxyl, halogen, nitro, acetyl, hydroxyl, amino, SCN, tri-$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$alkyl, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkylaminocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, Q is a partly saturated or saturated heterocyclic or heteroaromatic 8-, 9-, 10-, 11- or 12-membered fused bicyclic or tricyclic ring system where at least one carbonyl group may optionally be present and/or where the ring system is optionally mono- or polysubstituted identically or differently, and where the substituents may independently be selected from cyano, halogen, nitro, acetyl, hydroxyl, amino, SCN, tri-$(C_1-C_6)$-alkylsilyl, $(C_3-C_8)$-cycloalkyl, cyano-$(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$ alkynyloxy-$(C_1-C_4)$-alkyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-haloalkoxy-$(C_1-C_6)$-alkyl, $(C_2-C_6)$-alkenyloxy-$(C_1-C_6)$-alkyl, $(C_2-C_6)$-haloalkenyloxy-$(C_1-C_6)$-alkyl, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$ haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylcarbonyl-$(C_1-C_6)$-alkyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkyl-aminocarbonyl, di-$(C_1-C_6)$-alkyl-aminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkyl sulfoximino, aminothiocarbonyl, $(C_1-C_6)$-alkylaminothiocarbonyl, di-$(C_1-C_6)$-alkyl-aminothiocarbonyl, $(C_3-C_8)$-cycloalkylamino, NHCO—$(C_1-C_6)$-alkyl ($(C_1-C_6)$-alkylcarbonylamino), or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $NO_2$, $C_1-C_4$-alkoxy, $C_1-C_4$-haloalkoxy, n is 0, 1 or 2.

DETAILED DESCRIPTION OF A PREFERRED EMBODIMENT

It has additionally been found that the compounds of the formula (I) have very good efficacy as pesticides, preferably as insecticides and/or acaricides, and additionally generally have very good plant compatibility, in particular with respect to crop plants.

The compounds according to the invention are defined in general terms by the formula (I). Preferred substituents or ranges of the radicals given in the formulae mentioned above and below are illustrated hereinafter:

Configuration 2-1

Aa is preferably —C($R^8$)($R^9$)—,

Ab is preferably —C($R^{10}$)($R^{11}$)—,

Ac is preferably —C($R^{12}$)($R^{13}$)—,

Ad is preferably —C($R^{14}$)($R^{15}$)—, $R^1$ is preferably $(C_1-C_4)$alkyl, $(C_1-C_4)$hydroxyalkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyloxy-$(C_1-C_4)$alkyl, $(C_2-C_4)$haloalkynyl, $(C_2-C_4)$cyanoalkynyl, $(C_3-C_6)$cycloalkyl, $(C_3-C_6)$cycloalkyl($C_3-C_6$)cycloalkyl, $(C_1-C_4)$alkyl-$(C_3-C_6)$cycloalkyl, halo$(C_3-C_6)$cycloalkyl, $(C_1-C_4)$alkylamino, di-$(C_1-$ $C_4$)alkyl-amino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulfonylamino, $R^8$, $R^9$, $R^{10}$, $R^{11}$, $R^{12}$, $R^{13}$, $R^{14}$, $R^{15}$ are preferably independently hydrogen, cyano, halogen, nitro, acetyl, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano-($C_3$-$C_6$)-cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsultinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, aminothiocarbonyl, NHCO—($C_1$-$C_4$)alkyl (($C_1$-$C_4$)alkylcarbonylamino), and also preferably are phenyl or hetaryl, each of which is optionally mono- or disubstituted identically or differently, where (in the case of hetaryl) at least one carbonyl group may optionally be present and/or where possible substituents are in each case as follows: cyano, halogen, nitro, acetyl, amino, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsufonyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino), Q is preferably a heteroaromatic 8-, 9-, 10-, 11- or 12-membered fused bicyclic or tricyclic ring system, where at least one carbonyl group may optionally be present and/or where the ring system is optionally mono- or polysubstituted identically or differently and where the substituents may independently be selected from cyano, halogen, nitro, acetyl, hydroxyl, amino, SCN, tri-($C_1$-$C_6$)-alkylsilyl, ($C_3$-$C_8$)-cycloalkyl, cyano-($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_4$)-alkyl, ($C_2$-$C_6$)-haloalkynyl, ($C_1$-$C_6$)-alkoxy, ($C_1$-$C_6$)-haloalkoxy, ($C_1$-$C_6$)-haloalkoxy-($C_1$-$C_6$)-alkyl, ($C_2$-$C_6$)-alkenyloxy-($C_1$-$C_6$)-alkyl, ($C_2$-$C_6$)-haloalkenyloxy-($C_1$-$C_6$)-alkyl, ($C_1$-$C_6$) cyanoalkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$) alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkyl carbonyl —($C_1$-$C_6$)-alkyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), or where the substituents may independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n is preferably 0, 1 or 2.

Configuration 3-1

Aa is more preferably —C($R^8$)($R^9$)—,
Ab is more preferably —C($R^{10}$)($R^{11}$)—,
Ac is more preferably —C($R^{12}$)($R^{13}$)—,
Ad is more preferably —C($R^{14}$)($R^{15}$)—.

$R^1$ is more preferably ($C_1$-$C_4$)alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulfinyl-($C_1$-$C_4$)alkyl or ($C_1$-$C_4$)alkylsulfonyl-($C_1$-$C_4$)alkyl, $R^8$, $R^9$, $R^{10}$, $R^{11}$, $R^{12}$, $R^{13}$, $R^{14}$, $R^{15}$ are more preferably independently hydrogen, cyano, halogen, nitro, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano-($C_3$-$C_8$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfonyl, ($C_1$-$C_4$)alkylsulfonyl, ($C_1$-$C_4$)

haloalkylsulfonyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di-(C₁-C₄)alkylaminocarbonyl, (C₁-C₄)alkylsulfonylamino, (C₁-C₄)alkylamino, di-(C₁-C₄)alkylamino, aminosulfonyl, (C₁-C₄)alkylaminosulfonyl, di-(C₁-C₄)alkylaminosulfonyl, NHCO—(C₁-C₄)alkyl ((C₁-C₄)alkylcarbonylamino), and also more preferably are phenyl or hetaryl, each of which is optionally mono- or disubstituted identically or differently, where (in the case of hetaryl) at least one carbonyl group may optionally be present and/or where possible substituents are in each case as follows: cyano, halogen, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, (C₁-C₄)alkyl, (C₁-C₄)haloalkyl, (C₁-C₄)cyanoalkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₁-C₄)alkoxy, (C₁-C₄)haloalkoxy, (C₁-C₄)alkylhydroxyimino, (C₁-C₄)alkoxyimino, (C₁-C₄)alkyl-(C₁-C₄)alkoxyimino, (C₁-C₄)alkylthio, (C₁-C₄)haloalkylthio, (C₁-C₄)alkylsulfinyl, (C₁-C₄)haloalkylsulfinyl, (C₁-C₄)alkylsulfonyl, (C₁-C₄)haloalkylsulfonyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di-(C₁-C₄)alkylaminocarbonyl, (C₁-C₄)alkylsulfonylamino, (C₁-C₄)alkylamino, di-(C₁-C₄)alkylamino, aminosulfonyl, (C₁-C₄)alkylaminosulfonyl, di-(C₁-C₄)alkylaminosulfonyl, NHCO—(C₁-C₄)alkyl ((C₁-C₄)alkylcarbonylamino), Q is more preferably a heteroaromatic 9-membered or 12-membered fused bicyclic or tricyclic ring system from the group of Q1 to Q21,

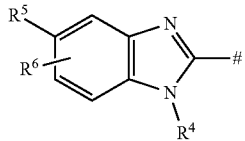

Q1

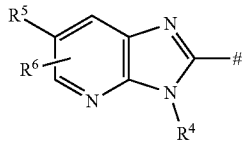

Q2

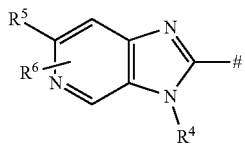

Q3

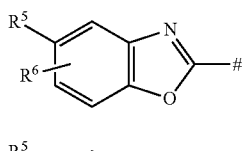

Q4

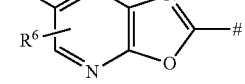

Q5

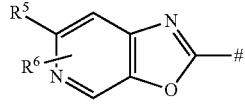

Q6

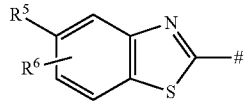

Q7

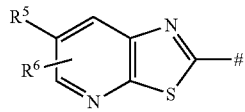

Q8

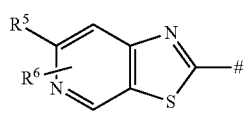

Q9

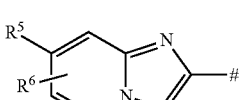

Q10

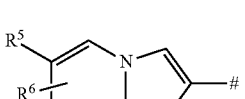

Q11

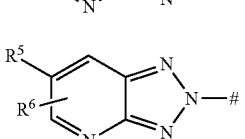

Q12

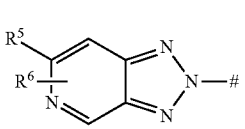

Q13

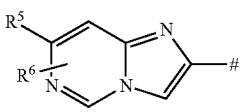

Q14

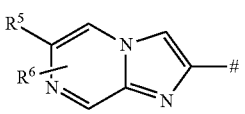

Q15

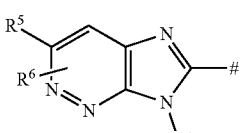

Q16

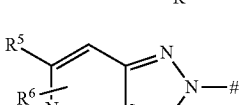

Q17

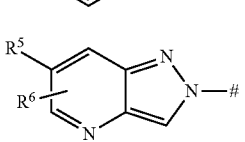

Q18

-continued

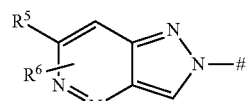
Q19

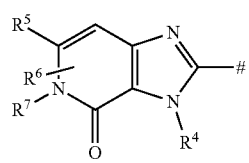
Q20

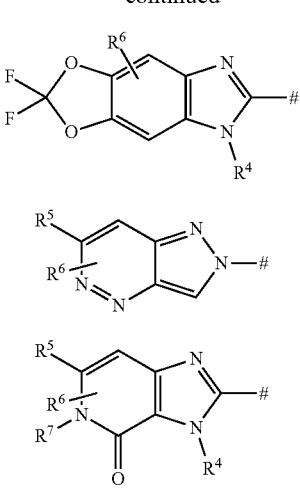
Q21

R⁴ is more preferably (C₁-C₁)-alkyl, (C₁-C₄)-haloalkyl, (C₁-C₄)-cyanoalkyl, (C₁-C₄)-hydroxyalkyl, (C₁-C₄)-alkoxy-(C₁-C₄)-alkyl, (C₁-C₄)-haloalkoxy-(C₁-C₄)-alkyl, (C₂-C₄)-alkenyl, (C₂-C₄)-alkenyloxy-(C₁-C₄)-alkyl, (C₂-C₄)-haloalkenyloxy-(C₁-C₄)-alkyl, (C₂-C₄)-haloalkenyl, (C₂-C₄)Cyanoalkenyl, (C₂-C₄)-alkynyl, (C₂-C₄)-alkynyloxy-(C₁-C₄)-alkyl, (C₂-C₄)-haloalkynyl, (C₃-C₆)-cycloalkyl, (C₃-C₆)-cycloalkyl-(C₃-C₆)-cycloalkyl, (C₁-C₄)-alkyl-(C₃-C₆)-cycloalkyl, halo-(C₃-C₆)-cycloalkyl, (C₁-C₄)-alkylthio-(C₁-C₄)-alkyl, (C₁-C₄)-alkylsulfinyl-(C₁-C₄)-alkyl, (C₁-C₄)-alkylsulfonyl-(C₁-C₄)-alkyl or (C₁-C₄)-alkylcarbonyl-(C₁-C₄)-alkyl, R⁵, R⁶ are independently more preferably hydrogen, cyano, halogen, (C₁-C₄)-alkyl, (C₁-C₄)-haloalkyl, (C₂-C₄)-alkenyl, (C₂-C₄)-haloalkenyl, (C₂-C₄)-alkynyl, (C₂-C₄)-haloalkynyl, (C₃-C₆)-cycloalkyl, cyano-(C₃-C₆)-cycloalkyl, (C₃-C₆)-cycloalkyl-(C₃-C₆)-cycloalkyl, (C₁-C₄)-alkyl-(C₃-C₆)-cycloalkyl, (C₁-C₄)-alkoxy, (C₁-C₄)-haloalkoxy, (C₁-C₄)-alkoxyimino, (C₁-C₄)-alkylthio, (C₁-C₄)-haloalkylthio, (C₁-C₄)-alkylsulfinyl, (C₁-C₄)-haloalkylsulfinyl, (C₁-C₄)-alkylsulfonyl, (C₁-C₄)-haloalkylsulfonyl, (C₁-C₄)-alkylsulfonyloxy, (C₁-C₄)-alkylcarbonyl, (C₁-C₄)-haloalkylcarbonyl, aminocarbonyl, (C₁-C₄)-alkylaminocarbonyl, di-(C₁-C₄)-alkylaminocarbonyl, (C₁-C₄)-alkylsulfonylamino, (C₁-C₄)-alkylamino, di-(C₁-C₄)-alkylamino, aminosulfonyl, (C₁-C₄)-alkylaminosulfonyl or di-(C₁-C₄)-alkylaminosulfonyl, R⁷ is more preferably hydrogen, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₁-C₄)haloalkoxy-(C₁-C₄)alkyl, (C₂-C₄)alkenyl, (C₂-C₄)alkenyloxy-(C₁-C₄)alkyl, (C₂-C₄)haloalkenyloxy-(C₁-C₄)alkyl, (C₂-C₄)haloalkenyl, (C₂-C₄)cyanoalkenyl, (C₂-C₄)alkynyl, (C₂-C₄)haloalkynyl, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, (C₁-C₄)alkylthio-(C₁-C₄)alkyl, (C₁-C₄)alkylsulfinyl-(C₁-C₄)alkyl or (C₁-C₄)alkylsulfonyl-(C₁-C₄)alkyl, n is more preferably 0, 1 or 2.

Configuration 4-1

Aa is even more preferably —C(R⁸)(R⁹)—,
Ab is even more preferably —C(R¹⁰)(R¹¹)—,
Ac is even more preferably —C(R¹²)(R¹³)—,
Ad is even more preferably —C(R¹⁴)(R¹⁵)—,
R¹ is even more preferably methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, R⁸, R⁹, R¹⁰, R¹¹, R¹², R¹³, R¹⁴, R¹⁵ are even more preferably independently hydrogen, cyano, halogen, (C₁-C₄)alkyl, (C₃-C₆)-cycloalkyl, cyano-(C₃-C₆)-cycloalkyl, (C₁-C₄)haloalkyl, (C₁-C₄)alkoxy, (C₁-C₄)haloalkoxy, (C₁-C₄)alkylthio, (C₁-C₄)alkylsulfinyl, (C₁-C₄)alkylsulfonyl, (C₁-C₄)haloalkylthio, (C₁-C₄)haloalkylsulfinyl, (C₁-C₄)haloalkylsulfonyl or NHCO—(C₁-C₄)alkyl ((C₁-C₄)alkylcarbonylamino), Q is even more preferably a heteroaromatic 9-membered or 12-membered fused bicyclic or tricyclic ring system from the group of Q2, Q3, Q4, Q10, Q11, Q14, Q15, Q16, Q19, Q20 or Q21,

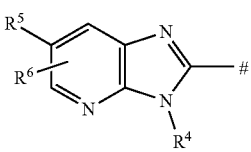
Q2

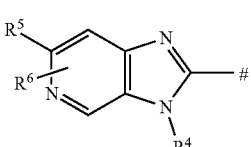
Q3

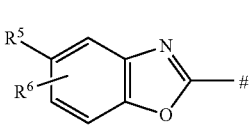
Q4

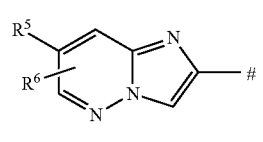
Q10

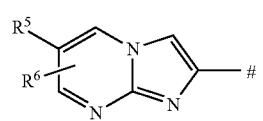
Q11

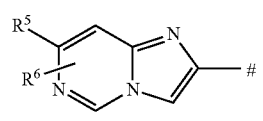
Q14

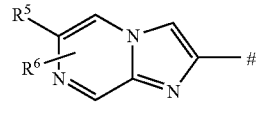
Q15

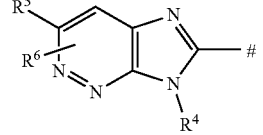
Q16

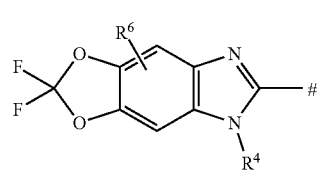
Q19

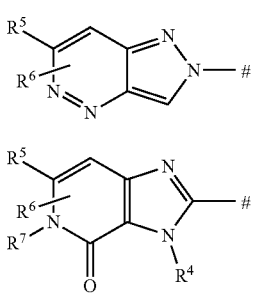
Q20

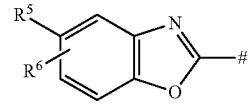
Q4

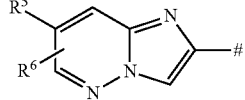
Q10

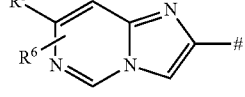
Q14

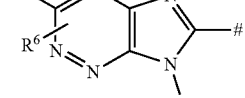
Q16

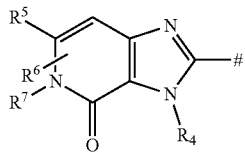
Q21

$R^4$ is even more preferably $(C_1-C_4)$-alkyl or $(C_1-C_4)$-alkoxy-$(C_1-C_4)$-alkyl, $R^5$ is even more preferably hydrogen, cyano, halogen, $(C_1-C_4)$alkyl, $(C_1-C_4)$haloalkyl, $(C_3-C_6)$cycloalkyl, cyano-$(C_3-C_6)$-cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylcarbonyl, $(C_1-C_4)$haloalkylcarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylaminosulfonyl or di-$(C_1-C_4)$alkylaminosulfonyl, $R^6$ is even more preferably hydrogen or methyl, $R^7$ is even more preferably hydrogen, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulfinyl-$(C_1-C_4)$alkyl or $(C_1-C_4)$alkylsulfonyl-$(C_1-C_4)$alkyl, n is even more preferably 0, 1 or 2.

Configuration 5-1

Aa is particularly —C($R^8$)($R^9$)—,
Ab is particularly —C($R^{10}$)($R^{11}$)—,
Ac is particularly —C($R^{12}$)($R^{13}$)—,
Ad is particularly —C($R^{14}$)($R^{15}$)—, $R^1$ is particularly methyl, ethyl, n-propyl, i-propyl or cyclopropyl, $R^8$, $R^9$, $R^{10}$, $R^{11}$, $R^{12}$, $R^{13}$, $R^{14}$, $R^{15}$ are particularly independently hydrogen, cyano, cyclopropyl, cyclobutyl, cyanocyclopropyl, fluorine, chlorine, bromine, methyl, ethyl, trifluoromethyl, difluoromethyl, trifluoroethyl, methoxy or ethoxy, Q is particularly a heteroaromatic 9-membered fused bicyclic ring system from the group of Q2, Q3, Q4, Q10, Q14, Q16 or Q21,

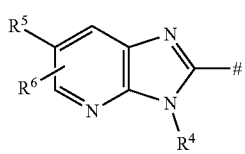
Q2

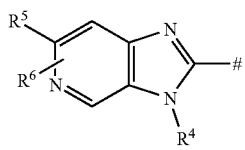
Q3

$R^4$ is particularly methyl, ethyl, isopropyl, methoxymethyl or methoxyethyl, $R^5$ is particularly fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulfinyl, trifluoromethylsulfonyl or cyanocyclopropyl, $R^6$ is particularly hydrogen, $R^7$ is particularly methyl, ethyl, isopropyl, cyclopropyl, methoxymethyl or methoxyethyl, n is particularly 0, 1 or 2.

Configuration 6-1

Aa is especially —C($R^8$)($R^9$)—,
Ab is especially —C($R^{10}$)($R^{11}$)—,
Ac is especially -C($R^{12}$)($R^{13}$)—,
Ad is especially —C($R^{14}$)($R^{15}$)—,
$R^1$ is especially ethyl,
$R^8$ is especially hydrogen,
$R^9$ is especially hydrogen,
$R^{10}$ is especially hydrogen or methyl,
$R^{11}$ is especially hydrogen,
$R^{12}$ is especially hydrogen, methyl or trifluoromethyl,
$R^{13}$ is especially hydrogen,
$R^{14}$ is especially hydrogen,
$R^{15}$ is especially hydrogen,
Q is especially a heteroaromatic 9-membered fused bicyclic ring system from the group of Q2 or Q3,
$R^4$ is especially methyl,
$R^5$ is especially trifluoromethyl, pentafluoroethyl, trifluoromethoxy, trifluoromethylthio, trifluoromethylsulfinyl or trifluoromethylsulfonyl,
$R^6$ is especially hydrogen,
n is especially 2.

Configuration 6-2

Aa is especially —C(R$^8$)(R$^9$)—,
Ab is especially —C(R$^{10}$)(R$^{11}$)—,
Ac is especially —C(R$^{12}$)(R$^{13}$)—,
Ad is especially —C(R$^{14}$)(R$^{15}$)—,
R$^1$ is especially ethyl,
R$^8$ is especially hydrogen,
R$^9$ is especially hydrogen,
R$^{10}$ is especially hydrogen, methyl or trifluoromethyl,
R$^{11}$ is especially hydrogen,
R$^{12}$ is especially hydrogen, methyl or trifluoromethyl,
R$^{13}$ is especially hydrogen,
R$^{14}$ is especially hydrogen,
R$^{15}$ is especially hydrogen,
Q is especially a heteroaromatic 9-membered fused bicyclic ring system from the group of Q2, Q3, Q4 or Q21,
R$^4$ is especially methyl,
R$^5$ is especially trifluoromethyl, pentafluoroethyl, trifluoromethoxy, trifluoromethylthio, trifluoromethylsulfinyl or trifluoromethylsulfonyl,
R$^6$ is especially hydrogen,
R$^7$ is especially methyl,
n is especially 2.

In a preferred embodiment, the invention relates to compounds of the formula (I) where Q is Q2 and Aa, Ab, Ac, Ad, R$^1$, R$^4$, R$^5$, R$^6$, R$^8$, R$^9$, R$^{10}$, R$^{11}$, R$^{12}$, R$^{13}$, R$^{14}$, R$^{15}$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where Q is Q3 and Aa, Ab, Ac, Ad, R$^1$, R$^4$, R$^5$, R$^6$, R$^8$, R$^9$, R$^{10}$, R$^{11}$, R$^{12}$, R$^{13}$, R$^{14}$, R$^{15}$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where Q is Q4 and Aa, Ab, Ac, Ad, R$^1$, R$^5$, R$^6$, R$^8$, R$^9$, R$^{10}$, R$^{11}$, R$^{12}$, R$^{13}$, R$^{14}$, R$^{15}$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where Q is Q21 and Aa, Ab, Ac, Ad, R$^1$, R$^4$, R$^5$, R$^6$, R$^7$, R$^8$, R$^9$, R$^{10}$, R$^{11}$, R$^{12}$, R$^{13}$, R$^{14}$, R$^{15}$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where R$^8$, R$^9$, R$^{10}$, R$^{11}$, R$^{12}$, R$^{13}$, R$^{14}$, R$^{15}$ are hydrogen and Q, Aa, Ab, Ac, Ad, R$^1$, R$^4$, R$^5$, R$^6$, R$^7$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where R$^8$, R$^9$, R$^{10}$, R$^{11}$, R$^{13}$, R$^{14}$, R$^{15}$ are hydrogen and R$^{12}$ is trifluoromethyl and Q, Aa, Ab, Ac, Ad, R$^1$, R$^4$, R$^5$, R$^6$, R$^7$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where R$^8$, R$^9$, R$^{10}$, R$^{11}$, R$^{13}$, R$^{14}$,
R$^{15}$ are hydrogen and R$^{12}$ is methyl and Q, Aa, Ab, Ac, Ad, R$^1$, R$^4$, R$^5$, R$^6$, R$^7$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where R$^8$, R$^9$, R$^{11}$, R$^{12}$, R$^{13}$, R$^{14}$, R$^{15}$ are hydrogen and R$^{10}$ is methyl and Q, Aa, Ab, Ac, Ad, R$^1$, R$^4$, R$^5$, R$^6$, R$^7$ and n have the definitions described in configuration (1-1) or configuration (2-1) or configuration (3-1) or configuration (4-1) or configuration (5-1) or configuration (6-1) or configuration (6-2).

In a preferred embodiment, the invention relates to compounds of the formula (I) where R$^8$, R$^9$, R$^{11}$, R$^{12}$, R$^{13}$, R$^{14}$, R$^{15}$ are hydrogen and R$^{10}$ is trifluoromethyl and Q, Aa, Ab, Ac, Ad, R$^1$, R$^4$, R$^5$, R$^6$, R$^7$ and n have the definitions described in configuration (1-1) or configuration (2-1) or configuration (3-1) or configuration (4-1) or configuration (5-1) or configuration (6-1) or configuration (6-2).

In the preferred definitions, unless stated otherwise,
halogen is selected from the group of fluorine, chlorine, bromine and iodine, preferably in turn from the group of fluorine, chlorine and bromine.
aryl (including as part of a larger unit, for example arylalkyl) is selected from the group of phenyl, benzyl, naphthyl, anthryl, phenanthrenyl, and is preferably in turn phenyl,
hetaryl (synonymous with heteroaryl, including as part of a larger unit, for example hetarylalkyl) is selected from the group of furyl, thienyl, pyrrolyl, pyrazolyl, imidazolyl, triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, pyridyl, pyrimidyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, log Puinolinyl, isolog Puinolinyl, cinnolinyl, phthalazinyl, log Puinazolinyl, log Puinoxalinyl, naphthyridinyl, benzotriazinyl, purinyl, pteridinyl and indolizinyl,
heterocyclyl is a saturated 4-, 5- or 6-membered ring containing 1 or 2 nitrogen atoms and/or one oxygen atom and/or one sulfur atom, for example azetidinyl, pyrrolidinyl, piperidinyl, oxetanyl, tetrahydrofuranyl, tetrahydropyranyl, dioxanyl, thietanyl, tetrahydrothiophenyl, tetrahydrothiopyranyl, piperazinyl, morpholinyl and thiomorpholinyl.

In the particularly preferred definitions, unless stated otherwise,
halogen is selected from the group of fluorine, chlorine, bromine and iodine, preferably in turn from the group of fluorine, chlorine and bromine.
aryl (including as part of a larger unit, for example arylalkyl) is selected from the group of phenyl, benzyl, naphthyl, anthryl, phenanthrenyl, and is preferably in turn phenyl,
hetaryl (including as part of a larger unit, for example hetarylalkyl) is selected from the group consisting of pyridyl, pyrimidyl, pyrazinyl, pyridazinyl, pyrazolyl, imidazolyl, triazolyl, thiazolyl and tetrazolyl,
heterocyclyl is selected from the group consisting of oxetanyl, tetrahydrofuryl and piperazinyl.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl.

Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood in the present case to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms may be identical or different. Halogen here is fluorine, chlorine, bromine or iodine, especially fluorine, chlorine or bromine.

Unless stated otherwise, optionally substituted radicals may be mono- or polysubstituted, where the substituents in the case of polysubstitutions may be the same or different.

The radical definitions or illustrations given in general terms or listed within ranges of preference apply correspondingly to end products and to starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Most preference according to the invention is given to using compounds of the formula (I) which contain a combination of the meanings listed above as being most preferable.

Especially used according to the invention are compounds of the formula (I) which contain a combination of the meanings listed above as being especially emphasized.

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

The inventive compounds of the formula (I) can be obtained by the processes shown in the following schemes:

Process A-1

The compounds of the formula (I) in which Q is Q1 to Q9, Q19 and Q21 can be prepared by known methods, for example analogously to the processes described in WO2009/131237, WO2010/125985, WO2011/043404, WO2011/040629, WO2012/086848, WO2013/018928, WO2015/000715, WO2015/121136, WO2016/124563, WO2016/124557, WO2017/001311, WO2017/001314, WO2017/061497, WO2017/084879, WO2017/089190, WO2017/133994.

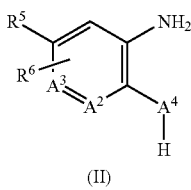
(II)

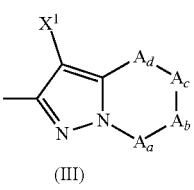
(III)

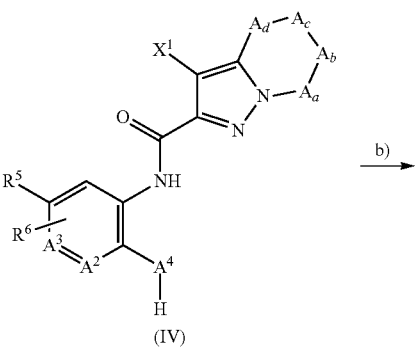
(IV)

-continued

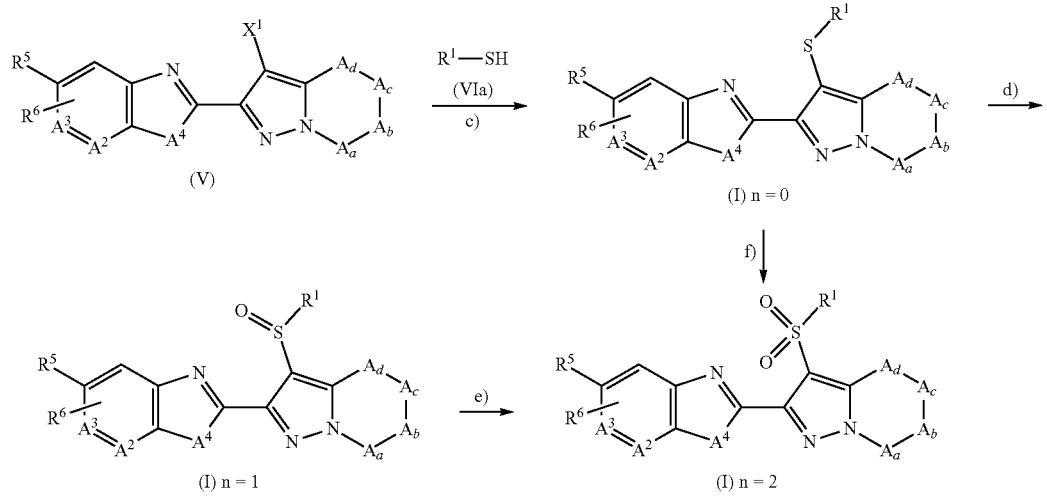

The radicals $R^1$, $R^4$, $R^5$, $R^6$, $R^7$, Aa, Ab, Ac, Ad and n have the definitions described above, $A^2$ and $A^3$ are CH or N, $A^4$ is O, S or N—$R^4$ and $X^1$ is halogen.

For compounds of the formula (I) in which Q is Q21, $A^2$ is carbonyl and $A^3$ is N—$R^7$.

Step a)

The compounds of the formula (IV) can be prepared in analogy to the process described in U.S. Pat. No. 5,576,335 by the reaction of compounds of the formula (II) with carboxylic acids of the formula (III) in the presence of a condensing agent or a base.

Compounds of the formula (II) are either commercially available or can be prepared by known methods, for example analogously to the processes described in US2003/69257, WO2006/65703, WO2009/131237, WO2010/125985, WO2011/043404, WO2011/040629, WO2012/086848, WO2013/018928, WO2015/000715, WO2016/091731, WO2016/142326, WO2016/169882, WO2016/23954 or WO2017/84879.

Carboxylic acids of the formula (III) are either commercially available or can be prepared by known methods. Possible preparation routes are described in process E.

The reaction of the compounds of the formula (II) with carboxylic acids of the formula (III) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be effected under reduced pressure, at standard pressure or under elevated pressure and at temperatures of 0° C. to 180° C.; with preference, the reaction is carried out at standard pressure and temperatures of 20 to 140° C.

Step b)

The compounds of the formula (V) can be prepared by condensing the compounds of the formula (IV), for example analogously to the processes described in WO2009/131237, WO2010/125985, WO2011/043404, WO2011/040629, WO2012/086848, WO2013/018928, WO2015/000715 or WO 2015/121136.

The conversion to compounds of the formula (V) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo (Hester, for example diethylazodicarboxylic acid.

Examples of suitable acids which can be used in the reaction described are sulfonic acids such as para-toluenesulfonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be conducted under reduced pressure, at standard pressure or under elevated pressure, and at temperatures of 0° C. to 200° C.

Step c)

The compounds of the formula (I) where n is 0 can be prepared by reacting the compounds of the formula (V) with the compounds of the formula (VIa) in the presence of a base.

Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (I) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

The reaction can be conducted under reduced pressure, at standard pressure or under elevated pressure, and at temperatures of 0° C. to 200° C.

In the reaction described, $X^1$ is preferably a fluorine or chlorine atom.

Another alternative, if $X^1$ is bromine or iodine, is transmetallation with a suitable lithium base and subselog Puent reaction with the appropriate commercially available disulfide; see Bioorganic and Medicinal Chemistry Letters, 20 (2010), 2770-2775.

In addition, if $X^1$ is bromine or iodine, it is possible to introduce the mercaptan derivative of the formula (VIa) with a suitable palladium catalyst, for example bis(dibenzylideneacetone)palladium(0) in the presence of a suitable ligand, for example 4,5-bis(diphenylphosphino)-9,9-dimethylxanthene (Xantphos), and in the presence of a suitable base, for example N,N-diisopropylethylamine, analogously to the processes described in JP2017/25059. The reaction is effected in a solvent, preferably in an ether, for example dioxane.

Step d)

The compounds of the formula (I) where n is 1 can be prepared by oxidizing the compounds of the formula (I) where n is 0. The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step e)

The compounds of the formula (I) where n is 2 can be prepared by oxidizing the compounds of the formula (I) where n is 1. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step f)

The compounds of the formula (I) where n is 2 can also be prepared in a one-step process by oxidizing the compounds of the formula (I) where n is 0. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Process A-2

The compounds of the formula (I) in which n is 2 and Q is Q1 to Q9, Q19 and Q21 can be prepared by known methods, for example analogously to the processes described in WO2009/131237, WO2010/125985, WO2011/043404, WO2011/040629, WO2012/086848, WO2013/018928, WO2015/000715 and WO2015/121136.

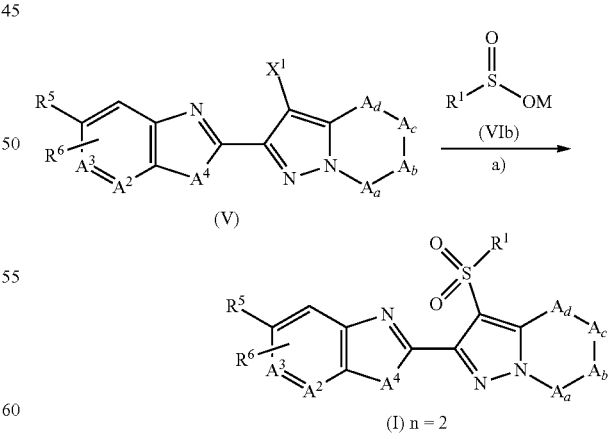

The $R^1$, $R^4$, $R^5$, $R^6$, $R^7$, Aa, Ab, Ac, Ad, $A^2$ and $A^3$ radicals have the definitions described above, $A^4$ is O, S or N—$R^4$ and $X^1$ is halogen, preferably bromine or iodine.

For compounds of the formula (I) in which Q is Q21, $A^2$ is carbonyl and $A^3$ is N—$R^7$.

Step a)

Alternatively, compounds of the formula (II) where n is 2 can also be prepared in a one-step procedure, for example in analogy to the process described in Journal of Organic Chemistry 2005, 70, 2696-2700 by a halogen-sulfone exchange with a compound of the formula (VIb) proceeding from compounds of the formula (V). The exchange is generally carried out in a solvent. Preference is given to using polar aprotic solvents, for example dimethyl sulfoxide and N,N-dimethylformamide.

Compounds of the formula (VIb) are either commercially available or can be prepared by known methods, for example analogously to the processes described in Organic Synthesis 1977, 57, 88-92; Tetrahedron Letters 1979, 9, 821-824 and Bulletin de la Societe Chimilog Pue de France 1958, 4, 447-450.

Examples of suitable sulfur reagents are the lithium, sodium or potassium salts of sulfinic acid.

The reaction can be conducted under reduced pressure, at standard pressure or under elevated pressure, and at temperatures of −20° C. to 120° C.

Process B

The compounds of the formula (I) in which Q represents Q10, Q11, Q14 or Q15 can be prepared by known methods, for example analogously to the processes described in US2009/203705, US2012/258951, WO2013/3298 or J. Med. Chem. 31, (1988) 1590-1595.

The radicals $R^1$, $R^5$, $R^6$, Aa, Ab, Ac, Ad and n have the definitions described above. $A^2$, $A^3$, $A^4$ and $A^5$ are CH or N (where $A^2$, $A^3$, $A^4$ and $A^5$ are not all N) and $X^1$ is halogen.

Step a)

Carboxylic acids of the formula (III) are converted in analogy to the process described in WO2015/107117, WO2011/75643 or EP2671582 in the presence of O,N-dimethylhydroxylamine hydrochloride to Weinreb amides of the formula (VI).

Carboxylic acids of the formula (III) are either commercially available or can be prepared by known methods. Possible preparation routes are described in process E.

Step b, c)

Compounds of the formula (VI) can then be converted by known methods, for example in analogy to the process described in WO2011/75643, with a Grignard reagent, for example methylmagnesium bromide, to ketones of the formula (VII). Compounds of the formula (VIII) are obtainable by subselog Puent halogenation analogously, for example, to the known method described in US2012/302573.

Step d)

The compounds of the formula (X) can be prepared by cyclizing the compounds of the formula (VIII) with amines of the formula (IX). The cyclization is effected, for example, in ethanol, acetonitrile or N,N-dimethylformamide by known methods in analogy to the processes described, for example, in WO2005/66177, WO2012/88411, WO2013/

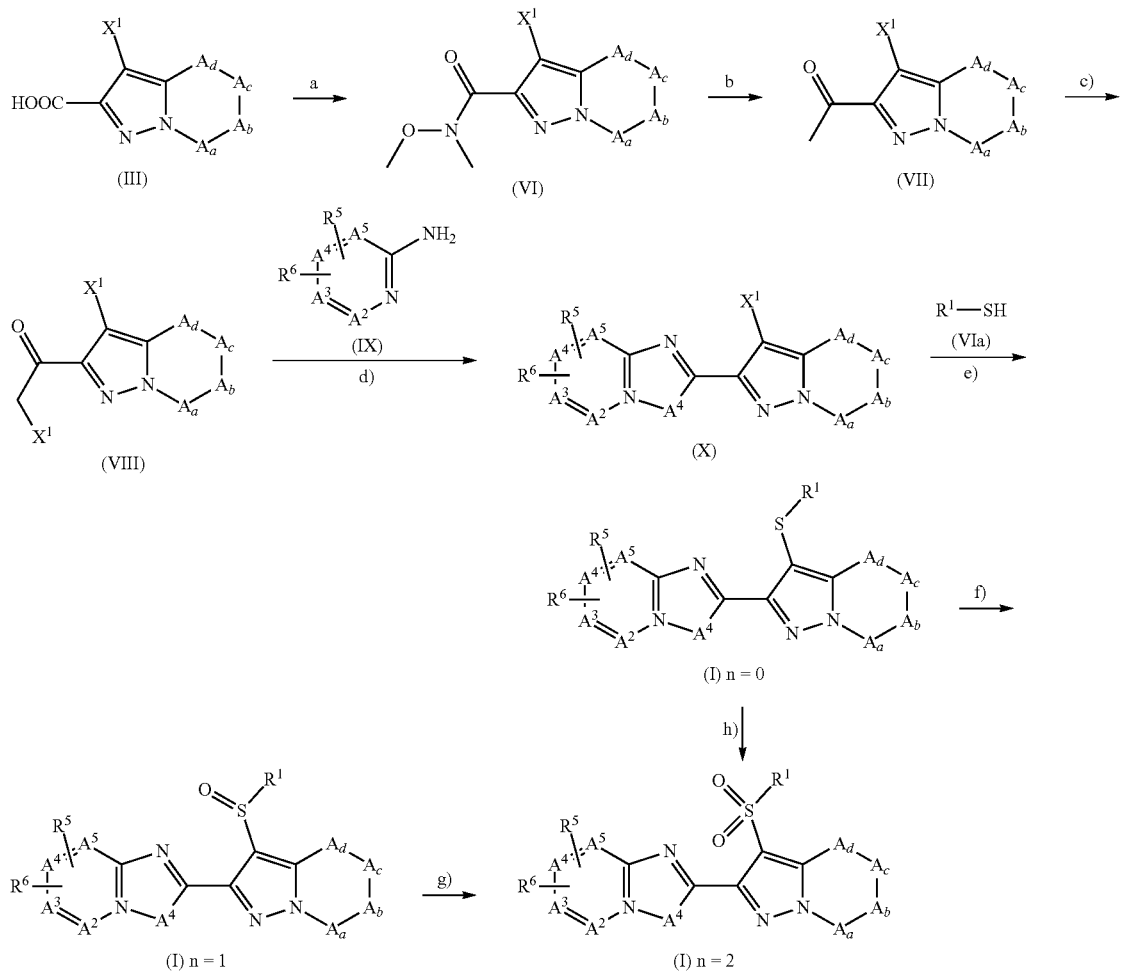

3298, US2009/203705, US2012/258951, WO2012/168733, WO2014/187762 or J. Med. Chem. 31 (1988) 1590-1595.

The compounds of the formula (IX) are commercially available.

Step e)

The compounds of the formula (I) where n is 0 can be prepared by reacting the compounds of the formula (X) with the compounds of the formula (VIa) in the presence of a base. Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

Another alternative, if $X^1$ is bromine or iodine, is transmetallation with a suitable lithium base and subselog Puent reaction with the appropriate commercially available disulfide; see Bioorganic and Medicinal Chemistry Letters, 20 (2010), 2770-2775.

In addition, if $X^1$ is bromine or iodine, it is possible to introduce the mercaptan derivative of the formula (VIa) with a suitable palladium catalyst, for example bis(dibenzylideneacetone)palladium(0) in the presence of a suitable ligand, for example 4,5-bis(diphenylphosphino)-9,9-dimethylxanthene (Xantphos), and in the presence of a suitable base, for example N,N-diisopropylethylamine, analogously to the processes described in JP2017/25059. The reaction is effected in a solvent, preferably in an ether, for example dioxane.

Step f, g)

The compounds of the formula (I) where n is 1 can be prepared by oxidizing the compounds of the formula (I) where n is 0. The oxidation is carried out by known methods using a suitable oxidizing agent, for example hydrogen peroxide, meta-chloroperbenzoic acid or sodium periodate.

The compounds of the formula (I) where n is 2 can be prepared by oxidizing the compounds of the formula (I) where n is 1.

The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Step h)

The compounds of the formula (I) where n is 2 can also be prepared in a one-step process by oxidizing the compounds of the formula (I) where n is 0. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Process C

The compounds of the formula (I) in which Q is Q16 can be prepared by known methods, for example analogously to the processes described in WO2014/142292.

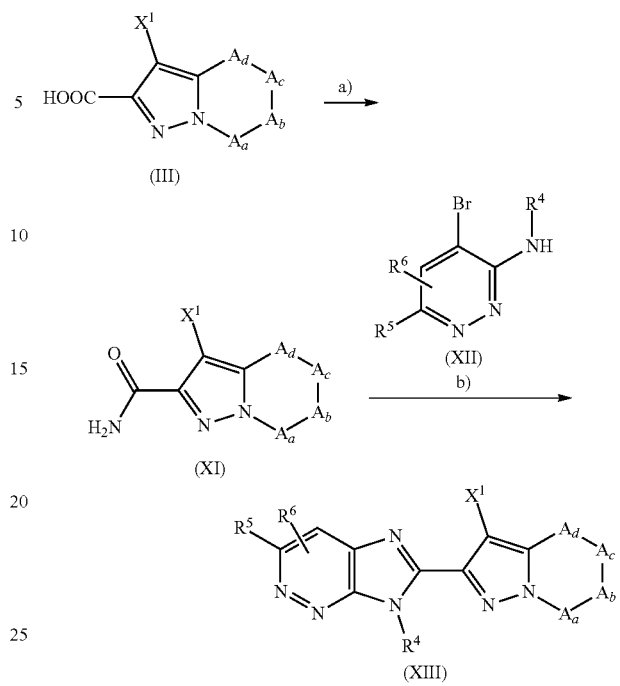

The $R^4$, $R^5$, $R^6$, Aa, Ab, Ac and Ad radicals have the definitions described above. $X^1$ is halogen.

Step a)

The compounds of the formula (XI) can be prepared in analogy to the process described in U.S. Pat. No. 5,374,646 or Bioorganic and Medicinal Chemistry Letters 2003, 13, 1093-1096 by reacting compounds of the formula (III) with an ammonia source in the presence of a condensing agent.

Carboxylic acids of the formula (III) are either commercially available or can be prepared by known methods. Possible preparation routes are described in process E.

In most cases, the ammonia source used is ammonium hydroxide.

The reaction of the compounds of the formula (III) with the ammonia source is preferably carried out in a solvent selected from customary solvents which are inert under the prevailing reaction conditions. Preference is given to ethers, for example dioxane or tetrahydrofuran.

A suitable condensing agent is, for example, carbonyldiimidazole.

The reaction can be carried out under reduced pressure, at atmospheric pressure or under elevated pressure. Preferably, the reaction is carried out at atmospheric pressure and temperatures from 20 to 70° C.

Step b)

The compounds of the formula (XIII) can be prepared in analogy to the process described in WO2014/142292 by reacting compounds of the formula (XI) with compounds of the formula (XII) in the presence of a palladium catalyst in basic media.

Compounds of the formula (XII) can be prepared, for example, analogously to the processes described in WO2014/142292. A palladium catalyst used may, for example, be [1,1'-bis-(diphenylphosphino)ferrocene]dichloropalladium(II). Frelog Puently, the bases used are inorganic bases such as potassium tert-butoxide.

The reaction is carried out in a solvent. Frelog Puently, toluene is used.

The reaction can be carried out under reduced pressure, at atmospheric pressure or under elevated pressure. Preferably, the reaction is carried out at atmospheric pressure and temperatures from 20 to 110° C.

The further conversion of compounds of the formula (XIII) to compounds of the formula (I) is carried out analogously to process A.

Process D

The compounds of the formula (I) in which Q represents Q12, Q13, Q17, Q18 or Q20 can be prepared by known methods, for example analogously to the processes described in WO2010/91310, WO2012/66061 or WO2013/99041.

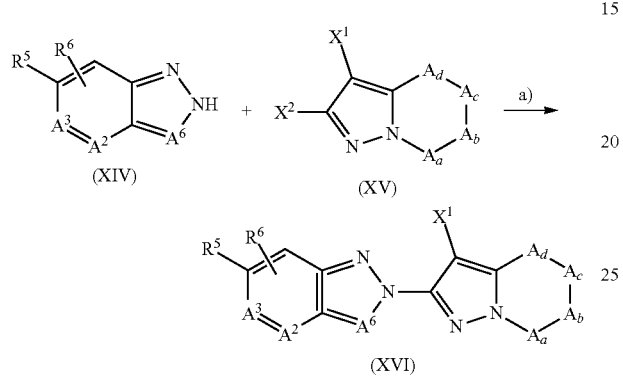

The $R^5$, $R^6$, Aa, Ab, Ac and Ad radicals have the definitions described above. $A^2$, $A^3$ and $A^6$ are CH or N (where $A^2$, $A^3$ and $A^6$ cannot simultaneously be N). $X^1$ and $X^2$ are halogen.

Step a)

The compounds of the formula (XVI) can be prepared by reacting compounds of the formula (XIV) with compounds of the formula (XV) under basic conditions, for example analogously to the processes described in WO2006/19831, WO2009/127686, Chem. Eur. J. 20 (2014), 974-978, WO2005/80388, WO2010/91310, WO2012/66061 or WO2013/99041.

Compounds of the formula (XIV) are either commercially available or can be prepared by known methods, for example analogously to the processes described in WO2005/100353, WO2012/66061 or in European Journal of Medicinal Chemistry 45 (2010), 2214-2222.

Compounds of the formula (XV) can be prepared by known methods, for example via an intermediate in which $X^2$ is halogen and $X^1$ is hydrogen, analogously to the processes described in WO2015/95788 or WO2015/95792. The subselog Puent conversion of $X^1$ from hydrogen to halogen is effected by known methods with a halogenating agent, for example N-chlorosuccinimide or N-bromosuccinimide, for example analogously to the processes described in Synthesis 47 (2015), 3221-3230, Bioorganic and Medicinal Chemistry Letters, 27 (2017) 4044-4050 or WO2011/50284.

The bases used are usually inorganic bases such as sodium hydride, potassium carbonate or caesium carbonate.

The conversion to compounds of the formula (XVI) is usually carried out in a solvent, preferably in a nitrile, for example acetonitrile or propionitrile, or in an aprotic polar solvent, for example N,N-dimethylformamide or N-methylpyrrolidone.

The reaction can be conducted under reduced pressure, at standard pressure or under elevated pressure, and at temperatures of 0° C. to 200° C.

Alternatively, the reaction of compounds of the formula (XIV) with compounds of the formula (XV) to give compounds of the formula (XVI) can also be carried out by palladium-catalysed N-arylation, e.g. analogously to the processes described in Angewandte Chemie Int. Ed. 2011, 50, 8944-8947.

The further conversion of compounds of the formula (XVI) to compounds of the formula (I) is carried out analogously to process A.

Process E

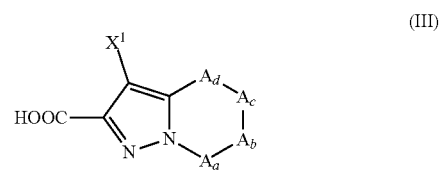

Carboxylic acids of the formula (III) are either commercially available or can be prepared by known methods, for example from pyridines of the formula (XVII) analogously to the processes described in WO2006/15737, WO2007/108750, US2009/186902, WO2009/23179, WO2009/095253, WO2010/34738, WO2010/91411, WO2011/15343, WO2011/41713, WO2011/50284, WO2014/14874, WO2016/12896 and Bioorganic and Medicinal Chemistry Letters, 22 (2012), 3460-3466.

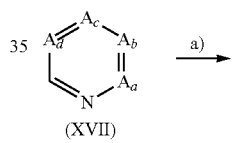

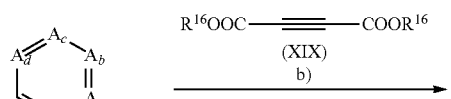

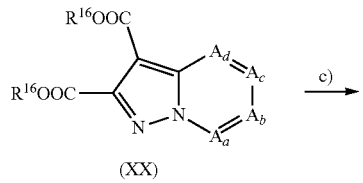

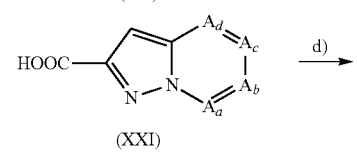

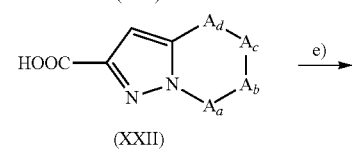

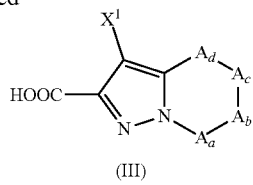

(III)

The Aa, Ab, Ac and Ad radicals have the definitions described above, X⁻ is a halide ion, preferably iodide, $X^1$ is halogen and $R^{16}$ is $(C_1-C_4)$alkyl.

Step a)

The compounds of the formula (XVIII) can be converted to an N-iminopyridinium intermediate in analogy to the processes described in WO2009/095253, WO2011/15343, WO2014/14874 or WO2010/34738 by reaction of compounds of the formula (XVII) with hydroxylamine-O-sulfonic acid in the presence of a base, for example potassium carbonate, and said intermediate is converted to the 1-aminopyridium derivative of the formula (XVIII) in a second step in the presence of an acid, for example hydriodic acid (HI), in a suitable solvent, for example ethanol. The pyridine derivatives of the formula (XVII) are commercially available.

Step b) and c)

Compounds of the formula (XX) can be prepared in analogy to the processes described in WO2009/095253, WO2011/15343, WO2014/14874 or WO2010/34738 from compounds of the formula (XVIII) in a 1,3-dipolar cycloaddition with an alkyne of the formula (XIX). If isomers are formed, these can be separated into the individual isomers by chromatographic methods. In this way, the diester of the formula (XX) can be obtained in isomerically pure form. By heating in a suitable acid, for example alog Pueous sulfuric acid, it is possible to convert compounds of the formula (XX) to acids of the formula (XXI) by decarboxylation and simultaneous hydrolysis of the ester function.

The compounds of the formula (XIX) are commercially available.

Step d)

Compounds of the formula (XXII) are either commercially available or can be synthesized in analogy to the processes described in WO2006/15737, WO2007/108750 or US2009/186902 via a hydrogenation of compounds of the formula (XXI).

Step e)

Compounds of the formula (III) can be prepared by known methods from compounds of the formula (XXII) via a halogenation, for example in analogy to the processes described in WO2009/23179, WO2010/91411, WO2011/41713, WO2011/50284, WO2016/12896 and Bioorganic and Medicinal Chemistry Letters, 22 (2012), 3460-3466, for example with N-chlorosuccinimide or N-bromosuccinimide as halogenating agent in a solvent, for example dimethylformamide, chloroform or acetonitrile.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable endotherm toxicity and good environmental compatibility, are suitable for protecting plants and plant organs against biotic and abiotic stress factors, for increasing harvest yields, for improving the log Puality of the harvested material and for controlling animal pests, especially insects, arachnids, helminths, especially nematodes and molluscs, which are encountered in agriculture, in horticulture, in animal husbandry, in alog Puatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropods, especially from the class of the Arachnids, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinse, Dermacentor* spp., *Eotetranychus* spp., e.g. *Eotetranychus hicoriae*, *Epitrimerus pyri*, *Eutetranychus* spp., e.g. *Eutetranychus banksi*, *Eriophyes* spp., e.g. *Eriophyes pyri*, *Glycyphagus domesticus*, *Halotydeus destructor*, *Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis*, *Nuphersa* spp., *Oligonychus* spp., e.g. *Oligonychus coffeae*, *Oligonychus coniferarum*, *Oligonychus ilicis*, *Oligonychus indicus*, *Oligonychus mangiferus*, *Oligonychus pratensis*, *Oligonychus punicae*, *Oligonychus yothersi*, *Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora*, *Platytetranychus multidigituli*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., e.g. *Tarsonemus confusus*, *Tarsonemus pallidus*, *Tetranychus* spp., e.g. *Tetranychus canadensis*, *Tetranychus cinnabarinus*, *Tetranychus turkestani*, *Tetranychus urticae*, *Trombicula alfreddugesi*, *Vaejovis* spp., *Vasates lycopersici*; from the class of the Chilopoda, for example *Geophilus* spp., *Scutigera* spp.;

from the order or the class of the Collembola, for example *Onychiurus armatus*; *Sminthurus viridis*; from the class of the Diplopoda, for example *Blaniulus guttulatus*;

from the class of the Insects, for example from the order of the Blattodea, e.g. *Blatta orientalis*, *Blattella asahinai*, *Blattella germanica*, *Leucophaea maderae*, *Loboptera decipiens*, *Neostylopyga rhombifolia*, *Panchlora* spp., *Parcoblatta* spp., *Periplaneta* spp., e.g. *Periplaneta americana*, *Periplaneta australasiae*, *Pycnoscelus surinamensis*, *Supella longipalpa*;

from the order of the Coleoptera, for example *Acalymma vittatum*, *Acanthoscelides obtectus*, *Adoretus* spp., *Aethina tumida*, *Agelastica alni*, *Agrilus* spp., for example *Agrilus planipennis*, *Agrilus coxalis*, *Agrilus bilineatus*, *Agrilus anxius*, *Agriotes* spp., for example *Agriotes linneatus*, *Agriotes mancus*, *Alphitobius diaperinus*, *Amphimallon solstitialis*, *Anobium punctatum*, *Anoplophora* spp., for example *Anoplophora glabripennis*, *Anthonomus* spp., for example *Anthonomus grundis*, *Anthrenus* spp., *Apion* spp., *Apogonia* spp., *Atomaria* spp., for example *Atomaria linearis*, *Attagenus* spp., *Bans caerulescens*, *Bruchidius obtectus*, *Bruchus* spp., for example *Bruchus pisorum*, *Bruchus rufimanus*, *Cassida* spp., *Cerotoma trifurcata*, *Ceutorrhynchus* spp., for example *Ceutorrhynchus assimilis*, *Ceutorrhynchus log Puadridens*, *Ceutorrhynchus rapae*, *Chaetocnema* spp., for example *Chaetocnema confinis*, *Chaetocnema denticulata*, *Chaetocnema ectypa*, *Cleonus mendicus*, *Conoderus* spp., *Cosmopolites* spp., for example *Cosmopolites sordidus*, *Costelytra zealundica*, *Ctenicera* spp., *Curculio* spp., for example *Curculio caryae*, *Curculio caryatrypes*, *Curculio obtusus*, *Curculio sayi*, *Cryptolestes ferrugineus*, *Cryptolestes pusillus*, *Cryptorhynchus lapathi*, *Cryptorhynchus mangiferae*, *Cylindrocopturus* spp., *Cylindrocopturus adspersus*, *Cylindrocopturus furnissi*, *Dendroctonus* spp., for example *Dendroctonus ponderosae*, *Dermestes* spp., *Diabrotica* spp., for example *Diabrotica balteata*, *Diabrotica barberi*, *Diabrotica undecimpunctata howardi*, *Diabrotica undecimpunctata undecimpunctata*, *Diabrotica virgifera virgifera*, *Diabrotica virgifera zeae*, *Dichocrocis* spp., *Dicladispa armigera*, *Diloboderus* spp., *Epicaerus* spp., *Epilachna* spp., for example *Epilachna borealis*, *Epilachna varivestis*, *Epitrix* spp., for example *Epitrix cucumeris*, *Epitrix fuscula*, *Epitrix hirtipennis*, *Epitrix subcrinita*, *Epitrix tuberis*, *Faustinus* spp., *Gibbium psylloides*, *Gnathocerus comutus*, *Hellula undalis*, *Heteronychus arator*, *Heteronyx* spp., *Hylamorpha elegans*, *Hylotrupes bajulus*, *Hypera postica*, *Hypomeces slog Puamosus*, *Hypothenemus* spp., for example *Hypothenemus hampei*, *Hypothenemus obscurus*, *Hypothenemus pubescens*, *Lachnosterna consanguinea*, *Lasioderma serricorne*, *Latheticus oryzae*, *Lathridius* spp., *Lema* spp., *Leptinotarsa decemlineata*, *Leucoptera* spp., for example *Leucoptera coffeella*, *Limonius ectypus*, *Lissorhoptrus oryzophilus*, *Listronotus* (=*Hyperodes*) spp., *Lixus* spp., *Luperodes* spp., *Luperomorpha xanthodera*, *Lyctus* spp., *Megacyllene* spp., for example *Megacyllene robiniae*, *Megascelis* spp., *Melanotus* spp., for example *Melanotus longulus oregonensis*, *Meligethes aeneus*, *Melolontha* spp., for example *Melolontha melolontha*, *Migdolus* spp., *Monochamus* spp., *Naupactus xanthographus*, *Necrobia* spp., *Neogalerucella* spp., *Niptus hololeucus*, *Oryctes rhinoceros*, *Oryzaephilus surinamensis*, *Oryzaphagus oryzae*, *Otiorhynchus* spp., for example *Otiorhynchus cribricollis*, *Otiorhynchus ligustici*, *Otiorhynchus ovatus*, *Otiorhynchus rugosostriarus*, *Otiorhynchus sulcatus*, *Oulema* spp., for example *Oulema melanopus*, *Oulema oryzae*, *Oxycetonia jucunda*, *Phaedon cochleariae*, *Phyllophaga* spp., *Phyllophaga helleri*, *Phyllotreta* spp., for example *Phyllotreta armoraciae*, *Phyllotreta pusilla*, *Phyllotreta ramose*, *Phyllotreta striolata*, *Popillia japonica*, *Premnotrypes* spp., *Prostephanus truncatus*, *Psylliodes* spp., for example *Psylliodes affinis*, *Psylliodes chrysocephala*, *Psylliodes punctulata*, *Ptinus* spp., *Rhizobius ventralis*, *Rhizopertha dominica*, *Rhynchophorus* spp., *Rhynchophorus ferrugineus*, *Rhynchophorus palmarum*, *Scolytus* spp., for example *Scolytus multistriatus*, *Sinoxylon perforans*, *Sitophilus* spp., for example *Sitophilus granarius*, *Sitophilus linearis*, *Sitophilus oryzae*, *Sitophilus zeamais*, *Sphenophorus* spp., *Stegobium paniceum*, *Sternechus* spp., for example *Sternechus paludatus*, *Symphyletes* spp., *Tanymecus* spp., for example *Tanymecus dilaticollis*, *Tanymecus indicus*, *Tanymecus palliatus*, *Tenebrio molitor*, *Tenebrioides mauretanicus*, *Tribolium* spp., for example *Tribolium audax*, *Tribolium castaneum*, *Tribolium confusum*, *Trogoderma* spp., *Tychius* spp., *Xylotrechus* spp., *Zabrus* spp., for example *Zabrus tenebrioides*;

from the order of the Dermaptera, for example *Anisolabis maritime*, *Forficula auricularia*, *Labidura riparia*;

from the order of the Diptera, for example *Aedes* spp., for example *Aedes aegypti*, *Aedes albopictus*, *Aedes sticticus*, *Aedes vexans*, *Agromyza* spp., for example *Agromyza frontella*, *Agromyza parvicornis*, *Anastrepha* spp., *Anopheles* spp., for example *Anopheles log Puadrimaculatus*, *Anopheles gambiae*, *Asphondylia* spp., *Bactrocera* spp., for example *Bactrocera cucurbitae*, *Bactrocera dorsalis*, *Bactrocera oleae*, *Bibio hortulanus*, *Calliphora erythrocephala*, *Calliphora vicina*, *Ceratitis capitata*, *Chironomus* spp., *Chrysomya* spp., *Chrysops* spp., *Chrysozona pluvialis*, *Cochliomya* spp., *Contarinia* spp., for example *Contarinia johnsoni*, *Contarinia nasturtil*, *Contarinia pyrivora*, *Contarinia schulzi*, *Contarinia sorghicola*, *Contarinia tritici*, *Cordylobia anthropophaga*, *Cricotopus sylvestris*, *Culex* spp., for example *Culex pipiens*, *Culex log Puinlog Puefasciatus*, *Culicoides* spp., *Culiseta* spp., *Cuterebra* spp., *Dacus oleae*, *Dasineura* spp., for example *Dasineura brassicae*, *Delia* spp., for example *Delia antilog Pua*, *Delia coarctata*, *Delia florilega*, *Delia platura*, *Delia radicum*, *Dermatobia hominis*, *Drosophila* spp., for example *Drosphila melanogaster*, *Drosophila suzukii*, *Echinocnemus* spp., *Euleia heraclei*, *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., for example *Liriomyza brassicae*, *Liriomyza huidobrensis*, *Liriomyza sativae*, *Lucilia* spp., for example *Lucilia cuprina*, *Lutzomyia* spp., *Mansonia* spp., *Musca* spp., for example *Musca domestics*, *Musca domestics vicina*, *Oestrus* spp., *Oscinella frit*, *Paratanytarsus* spp., *Paralauterborniella subcincta*, *Pegomya* or *Pegomyia* spp., for example *Pegomya betae*, *Pegomya hyoscyami*, *Pegomya rubivora*, *Phlebotomus* spp., *Phorbia* spp., *Phormia* spp., *Piophila casei*, *Platyparea poeciloptera*, *Prodiplosis* spp., *Psila rosae*, *Rhagoletis* spp., for example *Rhagoletis cingulata*, *Rhagoletis completa*, *Rhagoletis fausta*, *Rhagoletis indifferens*, *Rhagoletis mendax*, *Rhagoletis pomonella*, *Sarcophaga* spp., *Simulium* spp., for example *Simulium meridionale*, *Stomoxys* spp., *Tabanus* spp., *Tetanops* spp., *Tipula* spp., for example *Tipula paludosa*, *Tipula simplex*, *Toxotrypana curvicauda*;

from the order of the Hemiptera, for example *Acizzia acaciaebaileyanae*, *Acizzia dodonaeae*, *Acizzia uncatoides*, *Acrida turrita*, *Acyrthosipon* spp., e.g. *Acyrthosiphon pisum*, *Acrogonia* spp., *Aeneolamia* spp., *Agonoscena* spp., *Aleurocanthus* spp., *Aleyrodes proletella*, *Aleurolobus barodensis*, *Aleurothrixus floccosus*, *Allocaridara malayensis*, *Amrasca* spp., e.g. *Amrasca bigutulla*, *Amrasca devastans*, *Anuraphis cardui*, *Aonidiella* spp., e.g. *Aonidiella aurantii*, *Aonidiella citrina*, *Aonidiella inonnata*, *Aphanostigma piri*, *Aphis* spp., e.g. *Aphis citricola*, *Aphis craccivora*, *Aphis fabae*, *Aphis forbesi*, *Aphis glycines*, *Aphis gossypii*, *Aphis hederae*, *Aphis illinoisensis*, *Aphis middletoni*, *Aphis nasturtii*, *Aphis nerii*, *Aphis pomi*, *Aphis spiraecola*, *Aphis viburniphila*, *Arboridia apicalis*, *Arytainilla* spp., *Aspidiella* spp., *Aspidiotus* spp., e.g. *Aspidiotus nerii*, *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., e.g. *Cacopsylla pyricola*, *Calligypona marginata*, *Capulinia* spp., *Canneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris roses*, *Chromaphis juglandicola*, *Chrysomphalus aonidum*, *Chrysomphalus ficus*, *Cicadulina mbila*, *Coccomytilus halli*, *Coccus* spp., e.g. *Coccus hesperidum*, *Coccus longulus*, *Coccus pseudomagnoliarum*, *Coccus viridis*, *Cryptomyzus ribis*, *Cryptoneossa* spp., *Ctenarytaina* spp., *Dalbulus* spp., *Dialeurodes chittendeni*, *Dialeurodes citri*, *Diaphorina citri*, *Diaspis* spp., *Diuraphis* spp., *Doralis* spp., *Drosicha* spp., *Dysaphis* spp., e.g. *Dysaphis apiifolia*, *Dysaphis plantaginea*, *Dysaphis tulipae*, *Dysmicoccus* spp., *Empoasca* spp., e.g. *Empoasca abrupta*, *Empoasca fabae*, *Empoasca maligna*, *Empoasca solana*, *Empoasca stevensi*, *Eriosoma* spp., e.g. *Eriosoma americanum*, *Eriosoma lanigerum*, *Eriosoma pyricola*, *Erythroneura* spp., *Eucalyptolyma* spp., *Euphyllura* spp., *Euscelis bilobatus*, *Ferrisia* spp., *Fiorinia* spp., *Furcaspis oceanica*, *Geococcus coffeae*, *Glycaspis* spp., *Heteropsylla cubana*, *Heteropsylla spinulosa*, *Homalodisca coagulata*, *Hyalopterus arundinis*, *Hyalopterus pruni*, *Icerya* spp., e.g. *Icerya purchasi*, *Idiocerus* spp., *Idioscopus* spp., *Laodelphax striatellus*, *Lecanium* spp., e.g. *Lecanium comi* (=*Parthenolecanium corni*), *Lepidosaphes* spp., e.g. *Lepidosaphes ulmi*, *Lipaphis erysimi*, *Lopholeucaspis japonica*, *Lycorma delicatula*, *Macrosiphum* spp., e.g. *Macrosiphum euphorbiae*, *Macrosiphum lilii*, *Macrosiphum rosae*, *Macrosteles facifrons*, *Mahanarva* spp., *Melanaphis sacchari*, *Metcalfella* spp., *Metcalfa pruinosa*, *Metopolophium dirhodum*, *Monellia costalis*, *Monelliopsis pecanis*, *Myzus* spp., e.g. *Myzus ascalonicus*, *Myzus cerasi*, *Myzus ligustri*, *Myzus omatus*, *Myzus persicae*, *Myzus nicotianae*, *Nasonovia ribisnigri*, *Neomaskellia* spp., *Nephotettix* spp., e.g. *Nephotettix cincticeps*, *Nephotettix nigropictus*, *Nettigonicla spectra*, *Nilaparvata lugens*, *Oncometopia* spp., *Orthezia praelonga*, *Oxya chinensis*, *Pachypsylla* spp., *Parabemisia myricae*, *Paratrioza* spp., e.g. *Paratrioza cockerelli*, *Parlatoria* spp., *Pemphigus* spp., e.g. *Pemphigus bursarius*, *Pemphigus populivenae*, *Peregrinus maidis*, *Perkinsiella* spp., *Phenacoccus* spp., e.g. *Phenacoccus madeirensis*, *Phloeomyzus passerinii*, *Phorodon humuli*, *Phylloxera* spp., e.g. *Phylloxera devastatrix*, *Phylloxera notabilis*, *Pinnaspis aspidistrae*, *Planococcus* spp., e.g. *Planococcus citri*, *Prosopidopsylla flava*, *Protopulvinaria pyriformis*, *Pseudaulacaspis pentagona*, *Pseudococcus* spp., e.g. *Pseudococcus calceolariae*, *Pseudococcus comstocki*, *Pseudococcus longispinus*, *Pseudococcus maritimus*, *Pseudococcus viburni*, *Psyllopsis* spp., *Psylla* spp., e.g. *Psylla buxi*, *Psylla mali*, *Psylla pyri*, *Pteromalus* spp., *Pulvinaria* spp., *Pyrilla* spp., *Quadraspidiotus* spp., e.g. *Quadraspidiotus juglansregiae*, *Quadraspidiotus ostreaeformis*, *Quadraspidiotus pemiciosus*, *Quesada gigas*, *Rastrococcus* spp., *Rhopalosiphum* spp., e.g. *Rhopalosiphum maidis*, *Rhopalosiphum oxyacanthae*, *Rhopalosiphum padi*, *Rhopalosiphum rufiabdominale*, *Saissetia* spp., e.g. *Saissetia coffeae*, *Saissetia miranda*, *Saissetia neglects*, *Saissetia oleae*, *Scaphoideus titanus*, *Schizaphis graminum*, *Selenaspidus articulatus*, *Sipha flava*, *Sitobion avenge*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., e.g. *Toxoptera aurantii*, *Toxoptera citricidus*, *Trialeurodes vaporariorum*, *Trioza* spp., e.g. *Trioza diospyri*, *Typhlocyba* spp., *Unaspis* spp., *Viteus vitifolii*, *Zygina* spp.;

from the suborder of the Heteroptera, for example *Aelia* spp., *Anasa tristis*, *Antestiopsis* spp., *Boisea* spp., *Blissus* spp., *Calocoris* spp., *Campylomma livida*, *Cavelerius* spp., *Cimex* spp., e.g. *Cimex adjunctus*, *Cimex hemipterus*, *Cimex lectularius*, *Cimex pilosellus*, *Collaria* spp., *Creontiades dilutus*, *Dasynus piperis*, *Dichelops furcatus*, *Diconocoris hewetti*, *Dysdercus* spp., *Euschistus* spp., e.g. *Euschistus hems*, *Euschistus servus*, *Euschistus tristigmus*, *Euschistus variolarius*, *Eurydema* spp., *Eurygaster* spp., *Halyomorpha halys*, *Heliopeltis* spp., *Horcias nobilellus*, *Leptocorisa* spp., *Leptocorisa varicornis*, *Leptoglossus occidentalis*, *Leptoglossus phyllopus*, *Lygocoris* spp., e.g. *Lygocoris pabulinus*, *Lygus* spp., e.g. *Lygus elisus*, *Lygus hesperus*, *Lygus lineolaris*, *Macropes excavatus*, *Megacopta cribraria*, *Miridae*, *Monalonion atratum*, *Nezara* spp., e.g. *Nezara viridula*, *Nysius* spp., *Oebalus* spp., *Pentomidae*, *Piesma log Puadrate*, *Piezodorus* spp., e.g. *Piezodorus guildinii*, *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Hymenoptera, for example *Acromyrmex* spp., *Athalia* spp., e.g. *Athalia rosae*, *Atta* spp., *Camponotus* spp., *Dolichovespula* spp., *Diprion* spp., e.g. *Diprion similis*, *Hoplocampa* spp., e.g. *Hoplocampa cookei*, *Hoplocampa testudinea*, Lash's spp., *Linepithema* (*Iridiomyrmex*) *humile*, *Monomorium pharaonis*, *Paratrechina* spp., *Paravespula* spp., *Plagiolepis* spp., *Sirex* spp., for example *Sirex noctilis*, *Solenopsis invicta*, *Tapinoma* spp., *Technomyrmex albipes*, *Urocerus* spp., *Vespa* spp., e.g. *Vespa crabro*, *Wasmannia auropunctata*, *Xeris* spp.;

from the order of the Isopoda, for example *Armadillidium vulgare*, *Oniscus asellus*, *Porcellio scaber*;

from the order of the Isoptera, for example *Coptotermes* spp., e.g. *Coptotermes formosanus*, *Cornitermes cumulans*, *Cryptotermes* spp., *Incisitermes* spp., *Kalotermes* spp.,

*Microtermes obesi, Nasutitermes* spp., *Odontotermes* spp., *Porotermes* spp., *Reticulitermes* spp., e.g. *Reticulitermes flavipes, Reticulitermes hesperus*;

from the order of the Lepidoptera, for example *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographs* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia nigricana, Cydia pomonella, Dalaca noctuides, Diaphania* spp., *Diparopsis* spp., *Diatraea saccharalis, Dioryctria* spp., for example *Dioryctria zimmermani, Earias* spp., *Ecdytolopha aurantium, Elasmopalpus lignosellus, Eldana saccharins, Ephestia* spp., e.g. *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., e.g. *Euproctis chrysorrhoea, Euxoa* spp., *Feltia* spp., *Galleria mellonella, Gracillaria* spp., *Grapholitha* spp., e.g. *Grapholita molesta, Grapholita prunivora, Hedylepta* spp., *Helicoverpa* spp., e.g. *Helicoverpa armigera, Helicoverpa zea, Heliothis* spp., e.g. *Heliothis virescens Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., e.g. *Leucoptera coffeella, Lithocolletis* spp., e.g. *Lithocolletis blancardella, Lithophane antennata, Lobesia* spp., e.g. *Lobesia botrana, Loxagrotis albicosta, Lymantria* spp., e.g. *Lymantria dispar, Lyonetia* spp., e.g. *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., e.g. *Ostrinia nubilalis, Panolis flammea, Pannara* spp., *Pectinophora* spp., e.g. *Pectinophora gossypiella, Perileucoptera* spp., *Phthorimaea* spp., e.g. *Phthorimaea operculella, Phyllocnistis citrella, Phyllonorycter* spp., e.g. *Phyllonorycter blancardella, Phyllonorycter crataegella, Pieris* spp., e.g. *Pieris rapae, Platynota stultana, Plodia interpunctella, Plusia* spp., *Plutella xylostella* (=*Plutella maculipennis*), *Podesia* spp., for example *Podesia syringae, Prays* spp., *Prodenia* spp., *Protoparce* spp., *Pseudaletia* spp., e.g. *Pseudaletia unipuncta, Pseudoplusia includens, Pyrausta nubilalis, Rachiplusia nu, Schoenobius* spp., e.g. *Schoenobius bipunctifer, Scirpophaga* spp., e.g. *Scirpophaga innotata, Scotia segetum, Sesamia* spp., e.g. *Sesamia inferens, Sparganothis* spp., *Spodoptera* spp., e.g. *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tines cloacella, Tines pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., e.g. *Gryllotalpa gryllotalpa, Hieroglyphus* spp., *Locusts* spp., e.g. *Locusts migratoria, Melanoplus* spp., e.g. *Melanoplus devastator, Paratlanticus ussuriensis, Schistocerca gregaria*;

from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis, Ctenocephalides felis, Pulex irritans, Tunga penetrans, Xenopsylla cheopis*; from the order of the Thysanoptera, for example *Anaphothrips obscurus, Baliothrips biformis, Chaetanaphothrips leeuweni, Drepanothrips reuteri, Enneothrips flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci*;

from the order of the Zygentoma (=Thysanura), for example *Ctenolepisma* spp., *Lepisma saccharina, Lepismodes inlog Puilinus, Thermobia domestics*;

from the class of the Symphyla, for example *Scutigerella* spp., e.g. *Scutigerella immaculata*; pests from the phylum of the Molluscs, for example from the class of the *Bivalvia*, e.g. *Dreissena* spp.; and also from the class of the Gastropoda, for example *Arion* spp., e.g. *Arion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. plant-parasitic nematodes, in particular *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella omata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenge, Heterodera glycines, Heterodera schachtii, Hirschmaniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example

*Tylenchorhynchus annulatus, Tylenchulus* spp., for example *Tylenchulus semipenetrans, Xiphinema* spp., for example *Xiphinema index.*

The compounds of the formula (I) can, as the case may be, at certain concentrations or application rates, also be used as herbicides, safeness, growth regulators or agents to improve plant properties, as microbicides or gametocides, for example as fungicides, antimycotics, bactericides, virucides (including agents against viroids) or as agents against MIA (mycoplasma-like organisms) and RLO (rickettsia-like organisms). They can, as the case may be, also be used as intermediates or precursors for the synthesis of other active ingredients.

Formulations

The present invention further relates to formulations and use forms prepared therefrom as pesticides, for example drench, drip and spray lilog Puors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble lilog Puids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray lilog Puors or seed-dressing products).

Suitable extenders are, for example, water, polar and nonpolar organic chemical lilog Puids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), the esters (including fats and oils) and (poly)ethers, the simple and substituted amines, amides, lactams (such as N-alkylpyrrolidones) and lactones, the sulfones and sulfoxides (such as dimethyl sulfoxide), the carbonates and the nitriles.

If the extender used is water, it is also possible to use, for example, organic solvents as auxiliary solvents. Useful lilog Puid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, carbonates, for example propylene carbonate, butylene carbonate, diethyl carbonate or dibutyl carbonate, or nitriles such as acetonitrile or propanenitrile.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, carbonates such as propylene carbonate, butylene carbonate, diethyl carbonate or dibutyl carbonate, nitriles such as acetonitrile or propanenitrile, and water.

In principle, it is possible to use all suitable carriers. Suitable carriers include more particularly the following: e.g. ammonium salts and natural, finely ground rocks, such as kaolins, aluminas, talc, chalk, log Puartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use lilog Puefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), isethionate derivatives, phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste lilog Puors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, selog Puestrants, complexing agents, humectants, spreaders. In general, the compounds of the formula (I) can be combined with any solid or lilog Puid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally alog Pueous) application lilog Puor and/or from the spray coating into the cuticle of the plant and hence to increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the log Puality and/or the nutritional value of the harvested products, prolong storage life and/or improve the processibility of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used to improve plant properties, for example growth, yield and log Puality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, preferably carbamates selected from alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates selected from acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, log Puinalphos, sulfotep, tebupirimfos, temephos, terbufos, tetrachlorvinphos, thiometon, triazophos, triclorfon and vamidothion.

(2) GABA-gated chloride channel blockers, preferably cyclodiene-organochlorines selected from chlordane and endosulfan or phenylpyrazoles (fiproles) selected from ethiprole and fipronil.

(3) Sodium channel modulators, preferably pyrethroids selected from acrinathrin, allethrin, d-cis-trans allethrin, d-trans allethrin, bifenthrin, bioallethrin, bioallethrin 5-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, preferably neonicotinoids selected from acetamiprid, clothianidin, dinotefuran, imidacloprid, nitenpyram, thiacloprid and thiamethoxam, or nicotine, or sulfoximines selected from sulfoxaflor, or butenolides selected from flupyradifurone.

(5) Nicotinic acetylcholine receptor (nAChR) allosteric modulators, preferably spinosyns selected from spinetoram and spinosad.

(6) Glutamate-gated chloride channel (GluCl) allosteric modulators, preferably avermectins/milbemycins selected from abamectin, emamectin benzoate, lepimectin and milbemectin.

(7) Juvenile hormone mimetics, preferably juvenile hormone analogues selected from hydroprene, kinoprene and methoprene, or fenoxycarb or pyriproxyfen.

(8) Miscellaneous non-specific (multisite) inhibitors, preferably alkyl halides selected from methyl bromide and other alkyl halides, or chloropicrin or sulfuryl fluoride or borax or tartar emetic or methyl isocyanate generator selected from diazomet and metam.

(9) TRPV channel modulators of chordotonal organs selected from pymetrozine and pyriflulog Puinazone.

(10) Mite growth inhibitors selected from clofentezine, hexythiazox, diflovidazin and etoxazole.

(11) Microbial disruptors of the insect midgut membrane selected from *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins selected from Cry1Ab, Cry1Ac, Cry1Fa, Cry1A.105, Cry2Ab, Vip3A, mCry3A, Cry3Ab, Cry3Bb and Cry34 Ab1/35Ab1.

(12) Inhibitors of mitochondria) ATP synthase, preferably ATP disruptors selected from diafenthiuron, or organotin compounds selected from azocyclotin, cyhexatin and fenbutatin oxide or propargite or tetradifon.

(13) Uncouplers of oxidative phosphorylation via disruption of the proton gradient selected from chlorfenapyr, DNOC and sulfluramid.

(14) Nicotinic acetylcholine receptor channel blockers selected from bensultap, cartap hydrochloride, thiocyclam, and thiosultap-sodium.

(15) Inhibitors of chitin biosynthesis, type 0 selected from bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1 selected from buprofezin.

(17) Moulting disruptors (especially in the case of Diptera) selected from cyromazine.

(18) Ecdysone receptor agonists selected from chromafenozide, halofenozide, methoxyfenozide and tebufenozide.

(19) Octopamine receptor agonists selected from amitraz.

(20) Mitochondria) complex III electron transport inhibitors selected from hydramethylnon, acelog Puinocyl and fluacrypyrim.

(21) Mitochondria) complex I electron transport inhibitors, peferably METI acaricides selected from fenazalog Puin, fenpyroximate, pyrimidifen, pyridaben, tebufenpyrad and tolfenpyrad or rotenone (Derris).

(22) Voltage-dependent sodium channel blockers selected from indoxacarb and metaflumizone.

(23) Inhibitors of acetyl CoA carboxylase, preferably tetronic and tetramic acid derivatives selected from spirodiclofen, spiromesifen and spirotetramat.

(24) Mitochondria) complex IV electron transport inhibitors, preferably phosphines selected from aluminium phosphide, calcium phosphide, phosphine and zinc phosphide, or cyanides selected from calcium cyanide, potassium cyanide and sodium cyanide.

(25) Mitochondria) complex II electron transport inhibitors, preferably beta-keto nitrile derivatives selected from cyenopyrafen and cyflumetofen, or carboxanilides selected from pyflubumide.

(28) Ryanodine receptor modulators, preferably diamides selected from chlorantraniliprole, cyantraniliprole and flubendiamide.

(29) Modulators of chordotonal organs (with undefined target structure) selected from flonicamide.

(30) further active ingredients selected from afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometolog Puin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyriflulog Puinazon, pyriminostrobin, spirobudiclofen, tetramethylfluthrin, tetraniliprole, tetrachlorantraniliprole, tigolaner, tioxazafen, thiofluoximate, triflumezopyrim and iodomethane; additionally preparations based on *Bacillus firmus* (I-1582, BioNeem, Votivo), and the following compounds: 1-(2-fluoro-4-methyl-5-[(2,2,2-trifluoroethyl)sulfinyl]phenyl)-3-(trifluoromethyl)-1H-1,2,4-triazole-5-amine (known from WO2006/043635) (CAS 885026-50-6), (1'-[(2E)-3-(4-chlorophenyl)prop-2-en-1-yl]-5-fluorospiro [indole-3,4'-piperidine]-1(2H)-yl) (2-chloropyridin-4-yl)methanone (known from WO2003/106457) (CAS 637360-23-7), 2-chloro-N-[2-(1-[(2E)-3-(4- chlorophenyl)prop-2-en-1-yl]piperidin-4-yl)-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio]phenyl]amino]carbonyl]indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazole-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N-[4 (aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-ylcarboxylic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoroacetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoroacetamide (known from WO 2016005276 A1) (CAS 1689566-03-7), [N(Z)]—N-[1-[(6-chloro-3-pyridinyl)methyl]-2(1H)-pyridinylidene]-2,2,2-trifluoroacetamide (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Fungicides

The active ingredients specified herein by their common name are known and described, for example, in "Pesticide Manual" (16th Ed. British Crop Protection Council) or searchable on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) flulog Puinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1- chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenyl)-2-)trifluoromethyl)phenyl]-1-(1H-1,2,4-triazol-1-yl)butan-2-ol, (1.054) 2-[4-(4-chlorophenyl)-2-)trifluoromethyl)phenyl]-1-(1H-1,2,4-triazol-1-yl)butan-2-ol, (1.055) 2-[4-(4-chlorophenyl)-2-)trifluoromethyl)phenyl]-1-(1H-1,2,4-triazol-1-yl)butan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-([3-(1,1,2,2-tetrafluoroethoxy)phenyl]sulfanyl)phenyl)-N-ethyl-N-methylimidoformamide, (1.064) N'-(2,5-dimethyl-4-([3-(2,2,2-trifluoroethoxy)phenyl]sulfanyl)phenyl)-N-ethyl-N-methylimidoformamide, (1.065) N'-(2,5-dimethyl-4-([3-(2,2,3,3-tetrafluoropropoxy)phenyl]sulfanyl)phenyl)-N-ethyl-N-methylimidoformamide, (1.066) N'-(2,5-dimethyl-4-([3-(pentafluoroethoxy)phenyl]sulfanyl)phenyl)-N-ethyl-N-methylimidoformamide, (1.067) N'-(2,5-dimethyl-4-(3-[(1,1,2,2-tetrafluoroethyl)sulfanyl]phenoxy)phenyl)-N-ethyl-N-methylimidoformamide, (1.068) N'-(2,5-dimethyl-4-(3-[(2,2,2-trifluoroethyl)sulfanyl]phenoxy)phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-(3-[(pentafluoroethyl)sulfanyl]phenoxy)phenyl)-N-ethyl-N-methylimidoformamide, (1.071) N'-(2,5-dimethyl-4-phenoxyphenyl)-N-ethyl-N-methylimidoformamide, (1.072) N-(4-([3-(difluoromethoxy)phenyl]sulfanyl)-2,5-dimethylphenyl)-N-ethyl-N-methylimidoformamide, (1.073) N'-(4-(3-[(difluoromethyl)sulfanyl]phenoxy)-2,5-dimethylphenyl)-N-ethyl-N-methylimidoformamide, (1.074) N-[5-bromo-6-(2,3-dihydro-1H-inden-2-yloxy)-2-methylpyridin-3-yl]-N-ethyl-N-methylimidoformamide, (1.075) N'-(4-[(4,5-dichloro-1,3-thiazol-2-yl)oxy]-2,5-dimethylphenyl)-N-ethyl-N-methylimidoformamide, (1.076) N'-(5-bromo-6-[(1R)-1-(3,5-difluorophenyl)ethoxy]-2-methylpyridin-3-yl)-N-ethyl-N-methylimidoformamide, (1.077) N-(5-bromo-6-[(1S)-1-(3,5-difluorophenyl)ethoxy]-2-methylpyridin-3-yl)-N-ethyl-N-methylimidoformamide, (1.078) N'-{5 bromo-6-[(cis-4-isopropylcyclohexyl)oxy]-2-methylpyridin-3-yl}-N-ethyl-N-methylimidoformamide, (1.079) N-(5-bromo-6-[(trans-4-isopropylcyclohexyl)oxy]-2-methylpyridin-3-yl)-N-ethyl-N-methylimidoformamide, (1.080) N'-(5-bromo-6-[1-(3,5-difluorophenyl)ethoxy]-2-methylpyridin-3-yl)-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4- carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tat-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-[2-[(2,5-dimethylphenoxy)methyl]phenyl]-2-methoxy-N-methylacetamide, (3.025) (3S,6S,7R,8R)-8-benzyl-3-{([3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfde, (5.020) thiram, (5.021) zineb, (5.022) ziram, (5.023) 6-ethyl-5,7-dioxo-6,7-dihydro-5H-pynrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisolog Puinolin-1-yl)log Puinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-lone, (9.009) (2Z)-3-(4-tert-butylphenyl)-3-(2-chloropyridin-4-yl)-1-(morpholin-4-yl)prop-2-en-lone.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) prolog Puinazid, (13.005) log Puinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebuflolog Puin, (15.029) tecloftalam, (15.030) tolnifanide, (15.031) 1-(4-(4-[(5R)-5-(2,6-difluorophenyl)-4,5-dihydro-1,2-oxazol-3-yl]-1,3-thiazol-2-yl) piperidin-1-yl)-2-[5-methyl-3-(trifluoromethyl)-1H-pyrazol-1-yl]ethanone, (15.032) 1-(4-(4[(5S)-5-(2,6-difluorophenyl)-4,5-dihydro-1,2-oxazol-3-yl]-1,3-thiazol-2-yl)piperidin-1-yl)-2-[5-methyl-3-(trifluoromethyl)-1H-pyrazol-1-yl]ethanone, (15.033) 2-(6-benzylpyridin-2-yl)log Puinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-(5-[2-chloro-6-(prop-2-yn-1-yloxy)phenyl]-4,5-dihydro-1,2-oxazol-3-yl)-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-((5R)-3-[2-(1-([3,5-bis(difluoromethyl)-1H-pyrazol-1-yl]acetyl)piperidin-4-yl)-1,3-thiazol-4-yl]-4,5-dihydro-1,2-oxazol-5-yl)-3-chlorophenyl methanesulfonate, (15.040) 2-((5S) 3-[2-(1-([3,5-bis(difluoromethyl)-1H-pyrazol-1-yl]acetyl) piperidin-4-yl)-1,3-thiazol-4-yl]-4,5-dihydro-1,2-oxazol-5-yl)-3-chlorophenyl methanesulfonate, (15.041) 2-(2-[(7,8-difluoro-2-methyllog Puinolin-3-yl)oxy]-6-fluorophenyl)propan-2-ol, (15.042) 2-(2-fluoro-6-[(8-fluoro-2-methyllog Puinolin-3-yl)oxy]phenyl)propan-2-ol, (15.043) 2-(3-[2-(1-([3,5-bis(difluoromethyl)-1H-pyrazol-1-yl]acetyl)piperidin-4-yl)-1,3-thiazol-4-yl]-4,5-dihydro-1,2-oxazol-5-yl)-3-chlorophenyl methanesulfonate, (15.044) 2-(3-[2-(1-([3,5-bis(difluoromethyl)-1H-pyrazol-1-yl]acetyl)piperidin-4-yl)-1,3-thiazol-4-yl]-4,5-dihydro-1,2-oxazol-5-yl)phenyl methanesulfonate, (15.045) 2-phenylphenol and salts thereof, (15.046) 3-(4,4,5-trifluoro-3,3-dimethyl-3,4-dihydroisolog Puinolin-1-yl)log Puinoline, (15.047) 3-(4,4-difluoro-3,3-dimethyl-3,4-dihydroisolog Puinolin-1-yl)log Puinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(log Puinolin-3-yl)-2,3-dihydro-1,4-benzoxazepine, (15.055) but-3-yn-1-yl (6-[(([(Z)-(1-methyl-1H-tetrazol-5-yl)(phenyl)methylene]amino) oxy)methyl]pyridin-2-yl)carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) log Puinolin-8-ol, (15.060) log Puinolin-8-ol sulfate (2:1), (15.061) tert-butyl (6-[(([(1-methyl-1H-tetrazol-5-yl)(phenyl)methylene]amino) oxy)methyl]pyridin-2-yl)carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amylolilog Puefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B 30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penerrans*, *Pasteuria* spp. (*Rotylenchulus*

*reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V 117b, *Trichoderma atroviride*, in particular strain SC1 (Accession Number CBS 122089), *Trichoderma harzianum*, in particular *T. harzianum* nfai T39 (Accession Number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa anmigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include: *Agrobacterium* spp., *Azorhizobium caulinodans, Azospirillum* spp., *Azotobacter* spp., *Bradyrhizobium* spp., *Burkholderia* spp., insbesondere *Burkholderia cepacia* (ehemals bekannt als *Pseudomonas cepacia*), *Gigaspora* spp., oder *Gigaspora monosporum*, *Glomus* spp., *Laccaria* spp., *Lactobacillus buchneri, Paraglomus* spp., *Pisolithus tinctorus, Pseudomonas* spp., *Rhizobium* spp., insbesondere *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium* anthelminticum, chitin, Armour-Zen, Dryopteris filix-mas, Elog Puisetum *arvense*, Fortune Aza, Fungastop, Heads Up (*Chenopodium log Puinoa* saponin extract), pyrethrum/pyrethrins, Quassia *amara, Quercus*, Quillaja, Regalia, "Relog Puiem™ Insecticide", rotenone, ryania/ryanodine, Symphytum *officinale, Tanacetum vulgare*, thymol, Triact 70, TriCon, Tropaeulum *majus, Urtica dioica*, Veratrin, Viscum album, Brassicaceae extract, especially oilseed rape powder or mustard powder.

Safener as Mixing Components

The compounds of the formula (I) can be combined with safeners, for example benoxacor, clolog Puintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl) amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA technilog Pues. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher log Puality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryDTA, CryfB2, Cry9c, Cry2Ab, Cry3Bb and CryIF and also combinations thereof), and also increased resistance of the plants to phytopathogenic fungi, bacteria and/or viruses caused, for example, by systemic aclog Puired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in log Puestion may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, lilog Puid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frelog Puency and the application rate should be adjusted according to the level of infestation with the pest in log Puestion.

In the case of systemically active ingredients, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a lilog Puid form of the compounds of the formula (I), or by soil application, meaning that the compounds of the formula (I) according to the invention are introduced in solid form (e.g. in the form of granules) into the locus of the plants, or by drip application (often also referred to as "chemigation"), meaning that the inventive compounds of the formula (I) are introduced by means of surface or underground drip tubes over particular periods of time together with varying amounts of water at defined sites in the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or selog Puentially with a compound of the formula (I) and a mixing component. It further also comprises a method where the seed is treated at different times with a compound of the formula (I) and a mixing component.

The invention also relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis.*

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schadlingsbekampfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in alog Puaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or alog Puarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., Phtirus spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Wemeckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Muses* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Stemostoma* spp., *Tropilaelaps* spp., *Varroa* spp.; from the order of the Actinedida (Prostigmata), for example, *Acarapis* spp., *Cheyletiella* spp., *Demodex* spp., *Listrophorus* spp., *Myobia* spp., *Neotrombicula* spp., *Omithocheyletia* spp., *Psorergates* spp., *Trombicula* spp.; and from the order of the Acaridida (Astigmata), for example, *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example, *Giardia* spp., *Spironucleus* spp.

Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example, *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Illustrative helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antihelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or lilog Puid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active ingredients, especially with endo- and ectoparasiticides, are provided for the field of veterinary medicine.

In the field of animal health, "mixture" means not just that two (or more) different active ingredients are formulated in a common formulation and are correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in log Puestion.

The active ingredients specified here by their "common names" are known and are described, for example, in the "Pesticide Manual" (see above) or can be searched for on the Internet (e.g.: http://www.alanwood.net/pesticides).

Illustrative active ingredients from the group of the ectoparasiticides as mixing components include, without any intention that this should constitute a restriction, the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondria) ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondria) complex I electron transport inhibitors; (25) mitochondria) complex II electron transport inhibitors; (20) mitochondria) complex III electron transport inhibitors; (22) voltage-dependent sodium channel blockers; (23) inhibitors of acetyl CoA carboxylase; (28) ryanodine receptor modulators;

active ingredients having unknown or non-specific mechanisms of action, e.g. fentrifanil, fenoxacrim, cycloprene, chlorobenzilate, chlordimeform, flubenzimin, dicyclanil, amidoflumet, log Puinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, trigolaner, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive varroa acaricides, for example organic acids, e.g. formic acid, oxalic acid.

Illustrative active ingredients from the group of the endoparasiticides, as mixing components, include, but are not limited to, active anthelmintic ingredients and active antiprotozoic ingredients.

The active anthelmintic ingredients include but are not limited to the following active nematicidal, trematicidal and/or cestocidal compounds:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole; from the class of the depsipeptides, preferably cyclic depsipeptides, especially 24-membered cyclic depsipeptides, for example: emodepside, PF1022A;
from the class of the tetrahydropyrimidines, for example: morantel, pyrantel, oxantel;
from the class of the imidazothiazoles, for example: butamisole, levamisole, tetramisole;
from the class of the aminophenylamidines, for example: amidantel, deacylated amidantel (dAMD), tribendimidine;
from the class of the aminoacetonitriles, for example: monepantel;
from the class of the paraherlog Puamides, for example: paraherlog Puamide, derlog Puantel;
from the class of the salicylanilides, for example: tribromsalan, bromoxanide, brotianide, clioxanide, closantel, niclosamide, oxyclozanide, rafoxanide;
from the class of the substituted phenols, for example: nitroxynil, bithionol, disophenol, hexachlorophene, niclofolan, meniclopholan;
from the class of the organophosphates, for example: trichlorfon, naphthalofos, dichlorvos/DDVP, crufomate, coumaphos, haloxon;
from the class of the piperazinones/log Puinolines, for example: prazilog Puantel, epsiprantel; from the class of the piperazines, for example: piperazine, hydroxyzine;
from the class of the tetracyclines, for example: tetracycline, chlorotetracycline, doxycycline, oxytetracycline, rolitetracycline;
from various other classes, for example: bunamidine, niridazole, resorantel, omphalotin, oltipraz, nitroscanate, nitroxynil, oxamnilog Puin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include, but are not limited to, the following active ingredients:
from the class of the triazines, for example: diclazuril, ponazuril, letrazuril, toltrazuril;
from the class of the polyether ionophores, for example: monensin, salinomycin, maduramicin, narasin;
from the class of the macrocyclic lactones, for example: milbemycin, erythromycin;
from the class of the log Puinolones, for example: enrofloxacin, pradofloxacin;
from the class of the log Puinines, for example: chlorolog Puine;
from the class of the pyrimidines, for example: pyrimethamine;
from the class of the sulfonamides, for example: sulfalog Puinoxaline, trimethoprim, sulfaclozin;
from the class of the thiamines, for example: amprolium;
from the class of the lincosamides, for example: clindamycin;
from the class of the carbanilides, for example: imidocarb;
from the class of the nitrofurans, for example: nifurtimox;
from the class of the log Puinazolinone alkaloids, for example: halofuginone;
from various other classes, for example: oxamnilog Puin, paromomycin;
from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by moslog Puitoes).

Examples of vectors and the diseases or pathogens they transmit are:

1) Moslog Puitoes
*Anopheles*: malaria, filariasis;
*Culex*: Japanese encephalitis, filariasis, other viral diseases, transmission of other worms;
*Aedes*: yellow fever, dengue fever, further viral disorders, filariasis;
Simuliidae: transmission of worms, especially *Onchocerca volvulus;*
Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia* bungdorferi sensu lato., *Borrelia* duttoni, tick-borne encephalitis, Q fever (*Coxiella burnetii*), babesioses (*Babesia* cans *canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as moslog Puitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in log Puestion without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is elog Pually possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnids, from the orders Scorpiones, Araneae and Opiliones, from the classes Chilopoda and Diplopoda, from the class Insects the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, lilog Puid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

2-[3-Ethylsulfonyl-5-(trifluoromethyl)-4,5,6,7-tetrahydropyrazolo[1,5-a]pyridin-2-yl]-3-methyl-6-(trifluoromethyl)imidazo[4,5-b]pyridine (I-1)

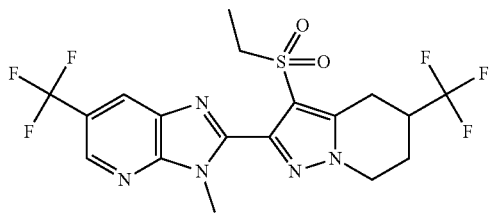 [SMILES: CCS(=O)(=O)c1c(-c2nc3cc(C(F)(F)F)cnc3n2C)nn2c1CC(C(F)(F)F)CC2]

265.0 mg (0.56 mmol) of 2-[3-bromo-5-(trifluoromethyl)-4,5,6,7-tetrahydropyrazolo[1,5-a]pyridin-2-yl]-3-methyl-6-(trifluoromethyl)imidazo[4,5-b]pyridine, 657.2 mg (5.66 mmol) of sodium ethanesulfinate and 16.2 mg (0.08 mmol) of copper(I) iodide were stirred in 15 ml of N,N-dimethylformamide in a microwave synthesis apparatus (Anton Paar, Monowave 400) at 120° C. for 12 hours (h). Subselog Puently, a sodium chloride solution was added to the reaction mixture and it was extracted with ethyl acetate. The organic phase was dried over sodium sulfate and then the solvent was distilled off under reduced pressure. The residue was purified by column chromatography purification via preparative HPLC with a water/acetonitrile gradient as eluent.

log P (HCOOH): 3.21; MW: 482; $^{1}$H NMR (400 MHz, DMSO-$d_6$) δ ppm: 1.26 (t, 3H), 2.18-2.22 (m, 1H), 2.33-2.37 (m, 1H), 3.00-3.06 (m, 1H), 3.19 (br. s, 1H), 3.47-3.53 (m, 1H), 3.75 (log P, 2H), 3.95 (s, 3H), 4.30-4.36 (m, 1H), 4.47-4.51 (m, 1H), 8.64 (s, 1H), 8.86 (s, 1H).

2-[3-Bromo-5-(trifluoromethyl)-4,5,6,7-tetrahydropyrazolo[1,5-a]pyridin-2-yl]-3-methyl-6-(trifluoromethyl)imidazo[4,5-b]pyridine

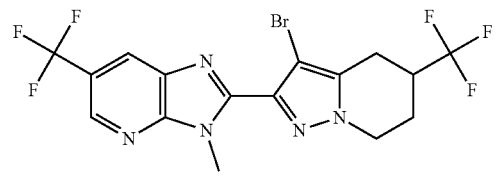 [SMILES: Cn1c(-c2nn3c(c2Br)CC(C(F)(F)F)CC3)nc2cc(C(F)(F)F)cnc21]

250 mg (1.30 mmol) of N2-methyl-5-(trifluoromethyl)pyridine-2,3-diamine, 502 mg (1.63 mmol) of 3-bromo-5-(trifluoromethyl)-4,5,6,7-tetrahydropyrazolo[1,5-a]pyridine-2-carboxylic acid and 251 mg (1.30 mmol) of 1-(3-dimethylaminopropyl)-3-ethylcarbodiimide hydrochloride (EDCI) were stirred in 10 ml of pyridine under argon at room temperature for 16 h. The reaction mixture was freed of the solvent under reduced pressure, water was added to the residue and it was extracted with ethyl acetate. The organic phase was dried over sodium sulfate and then the solvent was distilled off under reduced pressure. The residue was then stirred in 10 ml of concentrated acetic acid at 100° C. for 8 h. The mixture was diluted with water and extracted three times with ethyl acetate. The combined organic phases were washed with water and sodium hydrogencarbonate solution, the organic phase was removed and the water phase was extracted with ethyl acetate. The combined organic phases were dried over sodium sulfate and then the solvent was distilled off under reduced pressure.

log P (HCOOH): 3.99; MW: 468; $^{1}$H NMR (400 MHz, DMSO-$d_6$) δ ppm: 2.12-2.17 (m, 1H), 2.33-2.37 (m, 1H), 2.76-2.83 (m, 1H), 3.05-3.10 (m, 1H), 3.17 (br. s, 1H), 4.10 (s, 3H), 4.24-4.32 (m, 1H), 4.44-4.48 (m, 1H), 8.61 (s, 1H), 8.80 (s, 1H).

3-Bromo-5-(trifluoromethyl)-4,5,6,7-tetrahydropyrazolo[1,5-a]pyridine-2-carboxylic acid

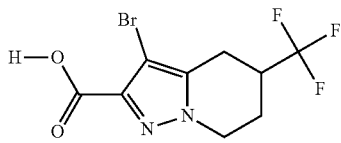 [SMILES: O=C(O)c1nn2c(c1Br)CC(C(F)(F)F)CC2]

881 mg (3.76 mmol) of 5-(trifluoromethyl)-4,5,6,7-tetrahydropyrazolo[1,5-a]pyridine-2-carboxylic acid and 337 mg (4.13 mmol) of N-bromosuccinimide were dissolved in 60 ml of chloroform and stirred at room temperature for 72 h. Water was added to the reaction mixture, the organic phase was removed and dried over sodium sulfate, and then the solvent was distilled off under reduced pressure.

log P (HCOOH): 1.75; MW: 313; $^1$H NMR (400 MHz, DMSO-$d_6$) δ ppm: 2.00-2.10 (m, 1H), 2.27-2.33 (m, 1H), 2.64-2.71 (m, 1H), 2.93-2.98 (m, 1H), 3.05-3.14 (s, 1H), 4.11-4.19 (m, 1H), 4.31-4.35 (m, 1H), 12.95 (br. s, 1H).

5-(Trifluoromethyl)-4,5,6,7-tetrahydropyrazolo[1,5-a]pyridine-2-carboxylic add

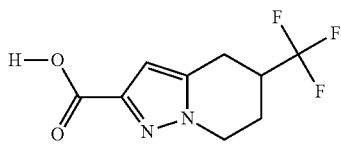 [SMILES: O=C(O)c1cc2n(n1)CCC(C(F)(F)F)C2]

1.00 g (4.34 mmol) of 5-(trifluoromethyl)pyrazolo[1,5-a]pyridine-2-carboxylic acid was hydrogenated in 65 ml of ethanol in the presence of 100 mg (0.44 mmol) of platinum (IV) oxide at 4 bar over the course of 12 h. Subselog Puently, the reaction mixture was filtered through Celite and washed through with ethanol, and the solvent was distilled off under reduced pressure.

log P (HCOOH): 1.28; MW: 235; $^1$H NMR (400 MHz, DMSO-$d_6$) δ ppm: 1.98-2.08 (m, 1H), 2.26-2.30 (m, 1H), 2.74-2.81 (m, 1H), 2.97-3.08 (m, 1H), 3.11-3.16 (s, 1H), 4.10-4.17 (m, 1H), 4.30-4.34 (m, 1H), 6.52 (s, 1H), 12.50 (br. s, 1H).

In analogy to the examples and by the preparation processes described above, it is possible to obtain the following compounds of the formula (I):

5-(Trifluoromethyl)pyrazolo[1,5-a]pyridine-2-carboxylic add

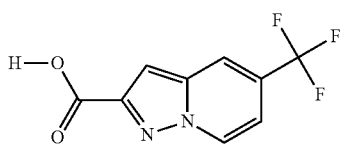 [SMILES: O=C(O)c1cc2cc(C(F)(F)F)ccn2n1]

2.00 g (6.61 mmol) of dimethyl 5-(trifluoromethyl)pyrazolo[1,5-a]pyridine-2,3-dicarboxylate were stirred in 50 ml of 50 percent sulfuric acid at 80° C. for 3 h. The cooled solution was alkalized with 5N sodium hydroxide solution while cooling with an ice bath and extracted with ethyl acetate. The aqueous phase was adjusted to pH 2-3 with 2N hydrochloric acid and diluted with water until dissolution was complete. The alog Pueous phase was extracted three times with ethyl acetate and dried over sodium sulfate, and then the solvent was distilled off under reduced pressure. The residue was purified by column chromatography purification via preparative HPLC with a water/acetonitrile mixture as eluent.

log P (HCOOH): 1.58; MW: 231; $^1$H NMR (400 MHz, DMSO-$d_6$) δ ppm: 7.29-7.32 (m, 2H), 8.36 (s, 1H), 8.93 (d, 1H), 13.4 (br. s, 1H).

Dimethyl 5-(trifluoromethyl)pyrazolo[1,5-a]pyridine-2,3-dicarboxylate

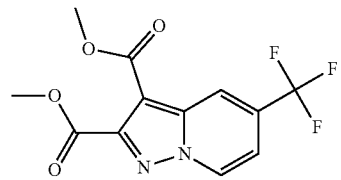 [SMILES: COC(=O)c1nn2ccc(C(F)(F)F)cc2c1C(=O)OC]

To an initial charge of 1.00 g (3.44 mmol) of 4-(trifluoromethyl)-1-aminopyridinium iodide and 953 mg (6.89 mmol) of potassium carbonate in 7 ml of dimethyl formamide were added dropwise, at room temperature, 514 mg (3.62 mmol) of dimethyl acetylenedicarboxylate. The reaction mixture was stirred at room temperature for 2 h, during which air was introduced. Subselog Puently, the mixture was filtered, the mother lilog Puor was removed and the solvent was distilled off under reduced pressure. The residue was taken up in water and extracted with ether. The organic phase was dried over sodium sulfate and then the solvent was distilled off under reduced pressure.

log P (HCOOH): 2.57; MW: 303; $^1$H NMR (400 MHz, DMSO-$d_6$) δ ppm: 3.89 (s, 3H), 3.95 (s, 3H), 7.57 (d, 1H), 8.38 (s, 1H), 9.15 (d, 1H).

4-(Trifluoromethyl)-1-aminopyridinium iodide

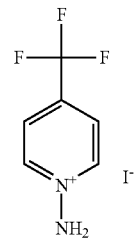

To an initial charge of 8.54 g (67.9 mmol) of hydroxylamine-O-sulfonic acid in 50 ml of water were added 10.00 g (67.9 mmol) of 4-(trifluoromethyl)pyridine. The mixture was stirred at 90° C. for 30 min and, after cooling, 9.395 g (67.9 mmol) of potassium carbonate were added. The residue was taken up in 85 ml of ethanol and filtered, and 9 ml of hydriodic acid (67.9 mmol, 57% strength) were added to the mother lilog Puor. After 14 h at −20° C., the precipitated solids were filtered off and converted further without further purification.

In analogy to the examples and by the preparation methods described above, it is possible to obtain the following compounds of the formula (I):

| Example | Structure |
|---|---|
| I-01 | 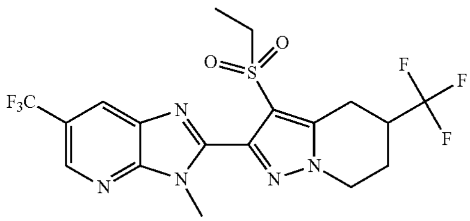 [SMILES: CCS(=O)(=O)c1c(-c2nc3cc(C(F)(F)F)cnc3n2C)nn2c1CC(C(F)(F)F)CC2] |
| I-02 | 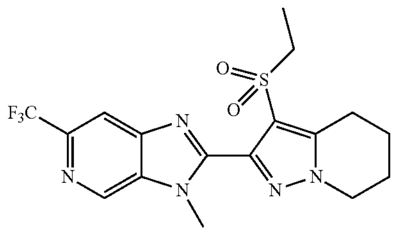 [SMILES: CCS(=O)(=O)c1c(-c2nc3cc(C(F)(F)F)ncc3n2C)nn2c1CCCC2] |
| I-03 | 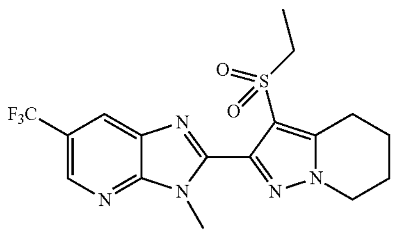 [SMILES: CCS(=O)(=O)c1c(-c2nc3cc(C(F)(F)F)cnc3n2C)nn2c1CCCC2] |
| I-04 | 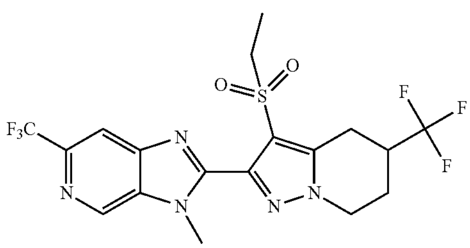 [SMILES: CCS(=O)(=O)c1c(-c2nc3cc(C(F)(F)F)ncc3n2C)nn2c1CC(C(F)(F)F)CC2] |
| I-05 | 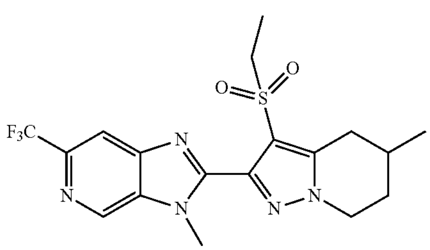 [SMILES: CCS(=O)(=O)c1c(-c2nc3cc(C(F)(F)F)ncc3n2C)nn2c1CC(C)CC2] |
| I-06 | 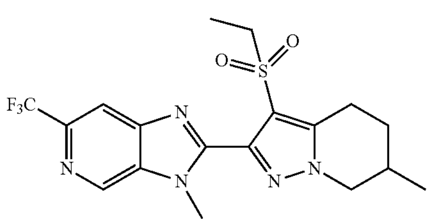 [SMILES: CCS(=O)(=O)c1c(-c2nc3cc(C(F)(F)F)ncc3n2C)nn2c1CCC(C)C2] |
| I-07 | |
| I-08 | |
| I-09 | |
| I-10 | |
| I-11 | |
| I-12 | |

| Example | Structure |
|---|---|
| I-13 | 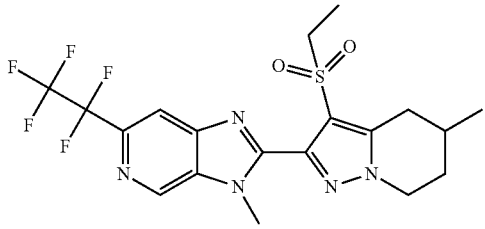 [SMILES: CCS(=O)(=O)c1c(-c2nc3cc(C(F)(F)C(F)(F)F)ncc3n2C)nn2c1CC(C)CC2] |
| I-14 | 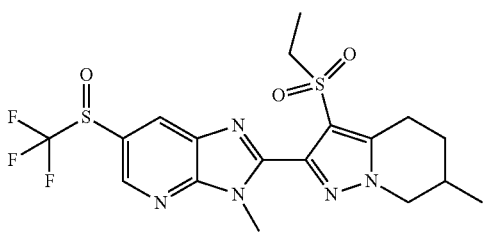 [SMILES: CCS(=O)(=O)c1c(-c2nc3cc(S(=O)C(F)(F)F)cnc3n2C)nn2c1CCC(C)C2] |
| I-15 | 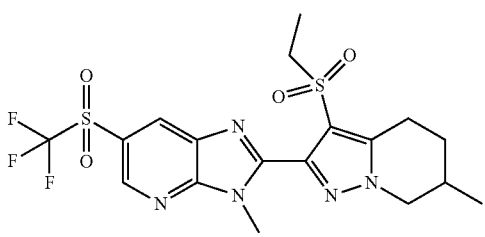 [SMILES: CCS(=O)(=O)c1c(-c2nc3cc(S(=O)(=O)C(F)(F)F)cnc3n2C)nn2c1CCC(C)C2] |
| I-16 | 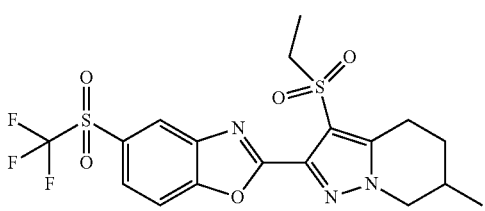 [SMILES: CCS(=O)(=O)c1c(-c2nc3cc(S(=O)(=O)C(F)(F)F)ccc3o2)nn2c1CCC(C)C2] |
| I-17 | 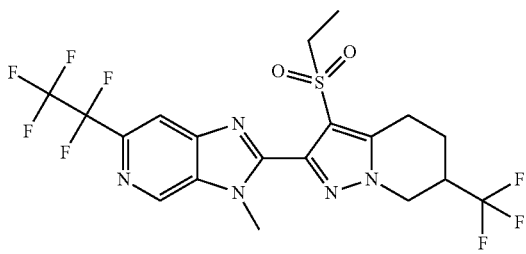 [SMILES: CCS(=O)(=O)c1c(-c2nc3cc(C(F)(F)C(F)(F)F)ncc3n2C)nn2c1CCC(C(F)(F)F)C2] |
| I-18 | 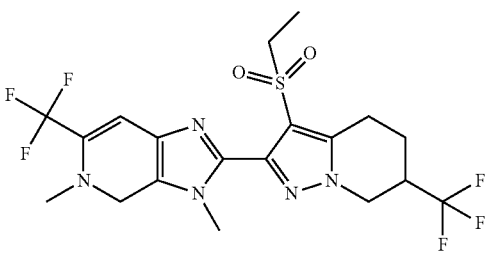 [SMILES: CCS(=O)(=O)c1c(-c2nc3c(n2C)CN(C)C(C(F)(F)F)=C3)nn2c1CCC(C(F)(F)F)C2] |

| Example | Structure |
|---|---|
| I-19 | 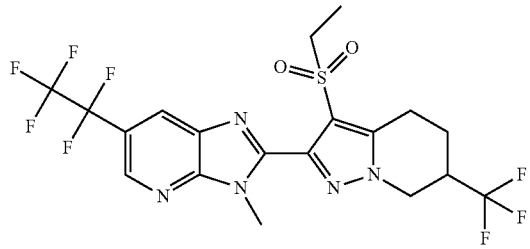 [SMILES: CCS(=O)(=O)c1c(-c2nc3cc(C(F)(F)C(F)(F)F)cnc3n2C)nn2c1CCC(C(F)(F)F)C2] |
| I-20 | 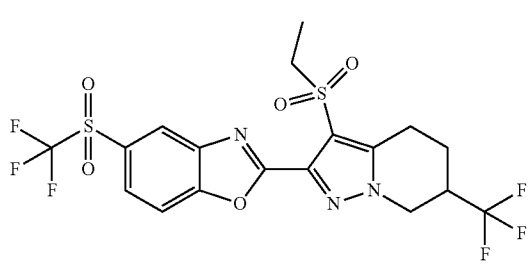 [SMILES: CCS(=O)(=O)c1c(-c2nc3cc(S(=O)(=O)C(F)(F)F)ccc3o2)nn2c1CCC(C(F)(F)F)C2] |

Analytical Determinations

The procedures for the analytical determinations described hereinafter relate to any information in the entire document if there is no separate description of the procedure for the particular analytical determination in the particular passage of text.

log P values

The log P values are measured according to EEC Directive 79/831 Annex V.A8 by HPLC (high-performance lilog Puid chromatography) on a reversed-phase column (C 18). Temperature: 55° C.

The LC-MS determination in the acidic range is effected at pH 2.7 with 0.1% alog Pueous formic acid and acetonitrile (containing 0.1% formic acid) as eluents; linear gradient from 10% acetonitrile to 95% acetonitrile. Called log P (HCOOH) in the table.

The LC-MS determination in the neutral range is effected at pH 7.8 with 0.001 molar alog Pueous ammonium hydrogencarbonate solution and acetonitrile as eluents; linear gradient from 10% acetonitrile to 95% acetonitrile. Called log P (neutral) in the table.

Calibration is effected using unbranched alkan-2-ones (having 3 to 16 carbon atoms) with known log P values (log P values determined on the basis of the retention times by linear interpolation between two successive alkanones).

Mass Spectrometry

The determination of [M+H]$^+$ or M$^-$ by means of LC-MS under acidic chromatographic conditions was conducted with 1 ml of formic acid per litre of acetonitrile and 0.9 ml of formic acid per litre of Millipore water as eluent. The Zorbax Eclipse Plus C18 50 mm*2.1 mm, 1.8 μm, column was used, at a column oven temperature of 55° C.

Instruments:

LC-MS3: Waters UPLC with SQD2 mass spectrometer and SampleManager autosampler. Linear gradient 0.0 to 1.70 minutes from 10% acetonitrile to 95% acetonitrile, from 1.70 to 2.40 minutes constant 95% acetonitrile, flow rate 0.85 ml/min.

LC-MS6 and LC-MS7: Agilent 1290 LC, Agilent MSD mass spectrometer, HTS PAL autosampler. Linear gradient 0.0 to 1.80 minutes from 10% acetonitrile to 95% acetonitrile, from 1.80 to 2.50 minutes constant 95% acetonitrile, flow rate 1.0 ml/min).

The determination of [M+H]⁺ by means of LC-MS under neutral chromatographic conditions was conducted with acetonitrile and Millipore water with 79 mg/l ammonium carbonate as eluent.

Instruments:

LC-MS4: Waters IClass Aclog Puity with QDA mass spectrometer and FIN autosampler (Waters Aclog Puity 1.7 μm 50 mm*2.1 mm column, column oven temperature 45° C.). Linear gradient 0.0 to 2.10 minutes from 10% acetonitrile to 95% acetonitrile, from 2.10 to 3.00 minutes constant 95% acetonitrile, flow rate 0.7 ml/min.

LC-MS5: Agilent 1100 LC System with MSD mass spectrometer and HTS PAL autosampler (column: Zorbax XDB C18 1.8 μm 50 mm*4.6 mm, column oven temperature 55° C.). Linear gradient 0.0 to 4.25 minutes from 10% acetonitrile to 95% acetonitrile, from 4.25 to 5.80 minutes constant 95% acetonitrile, flow rate 2.0 ml/min.

The retention time indices were determined in all cases from a calibration measurement of a homologous series of straight-chain alkan-2-ones having 3 to 16 carbons, where the index for the first alkanone was set to 300 and that for the last to 1600, and successive alkanones were interpolated in a linear manner between the values.

The measurements of the $^1$H NMR spectra were conducted with a Bruker Avance III 400 MHz spectrometer, elog Puipped with a 1.7 mm TCI probe head, with tetramethylsilane as standard (0.00 ppm), on solutions in the solvents $CD_3CN$, $CDCl_3$ or $d_6$-DMSO. Alternatively, a Bruker Avance III 600 MHz spectrometer elog Puipped with a 5 mm CPNMP probe head or a Bruker Avance NEO 600 MHz spectrometer elog Puipped with a 5 mm TCI probe head was used for the measurements. In general, the measurements were conducted at a probe head temperature of 298 K. If different measurement temperatures were used, this is noted separately.

NMR Data for Selected Examples

NMR Peak List Method

The 1H-NMR data of selected examples are noted in the form of 1H-NMR peak lists. For each signal peak, first the δ value in ppm and then the signal intensity in round brackets are listed. The pairs of δ value—signal intensity numbers for different signal peaks are listed with separation from one another by semicolons.

The peak list for one example therefore takes the form of:
$\delta_1$ (intensity$_1$); $\delta_2$ (intensity$_2$); ... ; $\delta_i$ (intensity$_i$); ... ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if relog Puired, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

Example

I-01 I-01: $^1$H-NMR (400.0 MHz, $d_6$-DMSO): δ=8.8634 (2.3); 8.8600 (2.3); 8.64 22 (2.4); 8.6381 (2.3); 4.5119 (0.4); 4.5032 (0.4); 4.4798 (0.6); 4.4711 (0.6); 4.3624 (0.4); 40.3513 (0.4); 4.3315 (0.6); 4.3210 (0.6); 4.3014 (0.4); 3.9466 (16.0); 3.7755 (0.9); 3.7571 (3.0); 3.7386 (3.1); 3.7202 (0.9); 3.5280 (0.6); 3.5159 (0.6); 3.4858 (0.7); 3.4731 (0.7); 3.3274 (227.4); 3.1916 (0.4); 3.1857 (0.4); 3.0643 (0.9); 3.0363 (0.6); 3.0212 (0.7); 20.9935 (0.5); 2.6758 (0.4); 2.6714 (0.6); 2.6670 (0.5); 2.5245 (1.6); 23109 (36.0); 2.5067 (76.0); 2.5023 (13.0); 2.4978 (75.6); 2.4936 (370.4); 2.3748 (0.4); 2.3392 (0.7); 2.3337 (0.8); 2.3291 (0.8); 2.3249 (03); 2.2211 (03); 2.2071 (0.6); 2.1886 (03); 2.1751 (0.4); 1.2733 (3.2); 1.2550 (7.3); 1.2364 (3.2); 0.0079 (1.6); −0.0002 (50.7); −0.0083 (2.2)

I-02 I-02: $^1$H-NMR (400.0 MHz, $d_6$-DMSO): δ=9.2242 (4.0); 8.3148 (0.4); 80.2511 (4.2); 4.2975 (13); 4.2823 (2.9); 4.2672 (13); 4.0245 (16.0); 3.6736 (1.0); 3.6553 (3.2); 3.6368 (3.3); 3.6184 (1.0); 3.3180 (112.0); 3.0924 (1.4); 3.0766 (3.0); 3.0607 (13); 2.6748 (1.1); 2.6704 (13); 2.6658 (1.2); 2.5098 (863); 2.5056 (177.3); 2.5011 (247.6); 2.4967 (196.4); 2.4926 (106.2); 2.3323 (1.0); 2.3280 (1.4); 2.3236 (1.1); 2.0758 (1.2); 2.0695 (1.6); 2.0594 (1.3); 2.0552 (1.3); 1.9027 (1.3); 1.8976 (1.3); 1.8880 (13); 1.8738 (1.1); 1.2421 (3.4); 1.2237 (7.6); 1.2052 (30.3); 0.1460 (0.7); 0.0176 (0.8); 0.0079 (6.3); −0.0002 (162.0); −0.0081 (11.2); −0.1497 (0.7)

I-03 I-03: $^1$H-NMR (400.0 MHz, $d_6$-DMSO): δ=8.8532 (2.4); 8.8500 (2.4); 8.6270 (2.4); 8.6232 (2.4); 4.3015 (1.4); 4.2865 (2.8); 4.2712 (13); 3.9304 (16.0); 3.7068 (0.9); 3.6884 (3.2); 3.6699 (3.2); 3.6515 (1.0); 3.3235 (49.0); 3.0973 (1.3); 3.0817 (2.9); 3.0657 (1.4); 2.8707 (03); 2.8594 (03); 2.6807 (0.3); 2.6761 (0.3); 2.6713 (0.4); 2.6666 (0.4); 2.5065 (44.4); 2.5022 (59.7); 2.4978 (44.2); 2.3289 (0.3); 2.0846 (1.0); 2.0703 (1.5); 2.0573 (1.2); 2.0409 (0.6); 1.9030 (1.3); 1.8883 (13); 1.8743 (1.1); 1.2485 (3.3); 1.2302 (7.4); 1.2117 (3.2); 0.0077 (1.2); −0.0002 (31.0); −0.0083 (1.4)

I-04 I-04: $^1$H-NMR (400.0 MHz, do-DMSO): δ=9.2338 (4.8); 9.2218 (2.6); 8.2658 (5.0); 8.2531 (2.7); 4.4947 (1.1); 4.4643 (1.6); 4.3438 (1.0); 4.3141 (1.6); 4.2826 (0.9); 40.1230 (0.3); 4.0398 (16.0); 4.0264 (8.3); 3.7431

(1.1); 3.7255 (3.7); 3.7073 (4.4); 3.6940 (2.4); 33185 (0.9); 3.5073 (1.4); 3.4768 (10.1); 3.4643 (1.6); 3.3176 (70.4); 3.3059 (47.4); 3.1830 (1.0); 3.0620 (1.5); 3.0335 (1.0); 3.0183 (13); 2.9911 (0.9); 2.6657 (1.4); 2.5005 (234.4); 2.4966 (246.4); 2.4935 (227.9); 2.3717 (1.2); 2.3282 (20.4); 2.2432 (0.4); 2.2300 (0.6); 2.2141 (1.0); 2.2002 (1.3); 2.1837 (1.2); 2.1694 (1.1); 2.1399 (0.4); 1.2862 (0.6); 1.2659 (4.0); 1.2479 (9.0); (5.8); 1.2159 (2.2); −0.0009 (590.4); −0.0037 (47.4); −0.0148 (25.6); −0.1501 (0.3)

I-05 I-05: $^1$H-NMR (400.0 MHz, d$_6$-DMSO): δ=9.2904 (0.4); 9.2240 (4.0); 8.3189 (0.4); 8.2511 (4.2); 4.4034 (0.5); 4.3957 (03); 4.3712 (0.8); 4.3633 (0.7); 4.2758 (0.4); 4.2653 (0.5); 4.2470 (0.6); 4.2359 (0.7); 4.2155 (0.4); 4.2027 (0.4); 40.0822 (1.6); 4.0566 (0.6); 4.0251 (16.0); 3.7194 (0.3); 3.7011 (0.4); 3.6765 (0.9); 3.6580 (2.6); 3.6394 (2.7); 3.6211 (0.9); 3.3243 (75.2); 3.2809 (0.7); 3.2696 (0.7); 2.6716 (0.3); 2.6120 (0.7); 2.5865 (0.8); 2.5673 (0.7); 2.5422 (0.8); 2.5244 (1.8); 23202 (10.6); 2.5107 (20.0); 2.5067 (42.0); 2.5022 (57.0); 2.4978 (42.8); 2.3288 (0.3); 2.0989 (0.8); 2.0728 (1.1); 2.0490 (0.7); 1.8309 (0.4); 10.8176 (0.5); 1.7979 (03); 1.7845 (0.4); 1.2427 (3.7); 1.2244 (8.3); 1.2058 (3.7); 1.1365 (5.0); 1.1204 (4.9); 0.0079 (1.1); −0.0002 (35.2); −0.0081 (2.1)

I-06 I-06: $^1$H-NMR (400.0 MHz, d$_6$-DMSO): δ=9.2242 (4.3); 8.3139 (0.4); 8.2519 (4.6); 4.4083 (0.8); 4.3974 (0.9); 4.3774 (0.9); 4.3639 (0.9); 4.0229 (16.0); 3.8560 (0.9); 3.8292 (1.2); 3.7970 (0.8); 3.7063 (03); 3.6881 (0.8); 3.6706 (10.7); 3.6522 (1.7); 3.6464 (1.7); 3.6282 (1.7); 3.6105 (0.9); 33924 (O0.4); 3.3259 (677.2); 3.2631 (0.8); 3.2307 (0.9); 3.0007 (0.4); 2.9839 (0.5); 2.9737 (0.5); 2.9554 (0.8); 2.9400 (0.4); 2.9269 (0.4); 20.9128 (0.4); 2.6751 (1.8); 2.6708 (2.2); 2.5058 (317.1); 2.5019 (398.8); 2.4980 (297.1); 2.3285 (2.4); 2.2437 (0.6); 2.2331 (0.7); 2.0003 (0.6); 1.9926 (0.6); 1.9652 (0.7); 1.5937 (0.3); 1.5788 (0.6); 13656 (0.6); 1.5469 (0.6); 1.5361 (0.5); 1.2388 (3.9); 1.2206 (7.8); 10.2022 (3.6); 1.1088 (6.2); 1.0923 (6.1); 0.1455 (0.4); −0.0002 (102.8); 0.1498 (0.6)

I-07 I-07: $^1$H-NMR (400.0 MHz, d$_6$-DMSO): δ=8.8528 (2.4); 8.8495 (2.4); 8.6248 (2.5); 8.6209 (2.4); 4.4127 (0.7); 4.3999 (0.8); 4.3800 (0.8); 4.3679 (0.8); 3.9298 (16.0); 3.8587 (0.8); 3.8316 (1.0); 3.8010 (0.8); 3.7416 (0.5); 3.7237 (0.7); 3.7064 (1.5); 3.6963 (0.5); 3.6879 (1.4); 3.6782 (1.4); 3.6697 (0.5); 3.6598 (1.5); 3.6426 (0.8); 3.6243 (0.4); 3.3201 (11.0); 3.2930 (0.6); 3.2853 (0.6); 3.2787 (0.6); 3.2720 (0.5); 3.2471 (0.5); 30.2393 (0.7); 3.2333 (0.7); 3.2267 (0.5); 3.0032 (0.4); 2.9871 (0.5); 20.9755 (0.5); 2.9586 (0.7); 2.9429 (0.3); 2.9307 (0.4); 2.6758 (0.4); 20.6712 (0.5); 2.5243 (1.2); 2.5065 (63.9); 2.5021 (83.5); 2.4977 (60.3); 2.3332 (0.4); 2.3288 (0.5); 2.3244 (0.4); 2.2457 (0.5); 1.9998 (0.5); 1.9922 (0.5); 1.9661 (0.6); 1.5812 (0.5); 1.5669 (0.6); 1.5475 (0.5); 1.5340 (0.5); 1.2457 (3.4); 1.2273 (7.5); 1.2088 (3.3); 1.1089 (5.8); 1.0923 (5.7); 0.0079 (0.9); −0.0002 (25.2)

I-08 I-08: $^1$H-NMR (400.0 MHz, d$_6$-DMSO): δ=8.7867 (2.2); 8.7820 (2.3); 8.5825 (2.3); 8.5780 (2.2); 4.4151 (0.6); 4.4019 (0.7); 4.3831 (0.7); 4.3703 (0.7); 3.9419 (16.0); 3.8613 (0.7); 3.8349 (0.9); 3.8034 (0.7); 3.7579 (0.5); 3.7398 (0.7); 3.7225 (1.4); 3.7040 (1.3); 3.6912 (1.3); 3.6728 (1.4); 3.6553 (0.7); 3.6375 (0.5); 3.3239 (123.8); 3.2927 (0.4); 3.2858 (0.5); 3.2799 (0.5); 3.2722 (0.4); 3.2479 (0.5); 3.2404 (0.6); 3.2345 (0.4); 30.2270 (0.5); 2.9878 (0.4); 2.9757 (0.5); 2.9590 (0.6); 2.6756 (0.4); 20.6710 (0.6); 2.6665 (0.4); 2.5244 (1.4); 2.5196 (2.1); 2.5109 (36.9); 2.5065 (77.9); 2.5020 (104.3); 20.4975 (74.4); 2.4931 (35.4); 2.3331 (0.4); 2.3288 (0.6); 2.3242 (0.4); 2.2490 (0.4); 1.9983 (0.4); 10.9909 (0.4); 1.9725 (0.4); 1.9657 (0.5); 1.5801 (0.4); 1.5661 (0.5); 13471 (0.5); 1.5339 (0.4); 1.2469 (3.2); 1.2285 (7.3); 1.2101 (3.1); 10.1078 (5.4); 1.0912 (5.3); −0.0002 (5.7)

I-09 I-09: $^1$H-NMR (400.0 MHz, d$_6$-DMSO): δ=8.5778 (2.0); 8.5721 (2.1); 8.3469 (1.9); 8.3436 (1.9); 4.4049 (0.6); 4.3925 (0.7); 4.3734 (0.8); 4.3606 (0.8); 3.9667 (0.3); 30.9010 (16.0); 3.8517 (0.8); 3.8252 (0.9); 3.7939 (0.7); 3.7441 (0.5); 3.7261 (0.8); 3.7088 (1.4); 3.6904 (1.4); 3.6772 (1.4); 3.6588 (1.5); 3.6414 (0.8); 3.6235 (0.5); 3.3239 (216.4); 3.2860 (0.5); 3.2797 (0.6); 3.2740 (0.6); 3.2667 (0.5); 3.2414 (0.5); 3.2344 (0.6); 30.2280 (0.6); 3.2214 (0.5); 2.9956 (0.3); 2.9800 (0.4); 2.9683 (0.4); 20.9507 (0.6); 2.9220 (0.3); 2.6756 (0.6); 2.6711 (0.8); 2.6667 (0.6); 20.5244 (1.9); 2.5108 (48.4); 2.5065 (101.0); 2.5021 (135.0); 2.4976 (980.2); 2.4935 (48.5); 2.3333 (0.6); 2.3288 (0.8); 2.3245 (0.6); 2.2391 (0.4); 2.2250 (0.4); 2.0019 (0.4); 1.9955 (0.4); 1.9887 (0.4); 10.9680 (0.5); 1.9612 (0.5); 1.5762 (0.4); 1.5618 (0.5); 1.5432 (0.5); 10.5297 (0.4); 1.2412 (3.3); 1.2228 (7.3); 1.2043 (3.2); 1.1056 (5.6); 10.0891 (5.5); 0.0078 (1.7); −0.0002 (530.7); −0.0080 (2.2)

I-10 I-10: $^1$H-NMR (400.0 MHz, d$_6$-DMSO): δ=8.8522 (2.3); 8.8487 (2.4); 8.6251 (2.4); 8.6203 (2.4); 8.3145 (0.4); 4.4071 (0.4); 4.3980 (0.5); 4.3738 (0.7); 4.3666 (0.7); 40.2788 (0.4); 4.2678 (0.5); 4.2515 (0.6); 4.2402 (0.6); 4.2195 (0.3); 30.9926 (1.5); 3.9631 (0.4); 3.9299 (16.0); 3.7564 (0.3); 3.7384 (0.4); 3.7076 (0.8); 3.6901 (2.1); 3.6697 (2.2); 3.6518 (0.8); 3.3192 (104.3); 3.2904 (0.7); 3.2780 (0.7); 2.8687 (0.4); 2.8572 (0.4); 2.6752 (1.1); 2.6707 (1.5); 2.6662 (1.2); 2.6139 (0.7); 2.5872 (0.8); 2.5681 (0.8); 2.5431 (1.1); 2.5239 (4.8); 2.5104 (93.2); 2.5061 (194.4); 2.5016 (260.8); 2.4972 (189.4); 2.4931 (93.4); 2.3328 (1.0); 2.3284 (1.5); 2.3241 (1.1); 2.0990 (0.8); 2.0738 (1.2); 20.0656 (1.0); 2.0501 (0.6); 1.8343 (0.4); 1.8212 (0.5); 1.8013 (0.4); 10.7919 (0.4); 1.2479 (3.5); 1.2296 (7.8); 1.2112 (3.4); 1.1368 (4.8); 10.1209 (4.9); 1.1073 (0.6); 0.0080 (0.3); −0.0002 (11.2)

I-11 I-11: $^1$H-NMR (400.0 MHz, d$_6$-DMSO): δ=8.7291 (2.7); 8.7244 (3.0); 8.6054 (2.7); 8.6008 (2.6); 4.4096 (0.6); 4.3967 (0.7); 4.3773 (0.8); 4.3649 (0.7); 3.9820 (0.4); 30.9149 (16.0); 3.8561 (0.7); 3.8291 (0.9); 3.7983 (0.7); 3.7451 (0.5); 3.7270 (0.8); 3.7098 (1.4); 3.6914 (1.4); 3.6796 (1.4); 3.6733 (0.5); 3.6612 (1.4); 3.6438 (0.8); 3.6259 (0.5); 3.3231 (81.1); 3.2898 (0.5); 3.2837 (0.5); 3.2767 (0.5); 3.2688 (0.4); 3.2443 (0.5); 30.2372 (0.6); 3.2312 (0.6); 3.2244 (0.5); 2.9988 (0.4); 2.9834 (0.4); 20.9709 (0.4); 2.9551 (0.6); 2.9267 (0.3); 2.6757 (0.4); 2.6711 (0.5); 20.6667 (0.4); 2.5243 (1.6); 2.5109 (31.5); 2.5066 (64.5); 23021 (85.4); 2.4976 (62.4); 2.4933 (31.1); 2.3332 (0.4); 2.3289 (0.5); 2.3242 (0.4); 2.2522 (0.4); 2.2432 (0.4); 1.9954 (0.4); 1.9892 (0.4); 10.9688 (0.5); 1.9631 (0.5); 1.5778 (0.4); 1.5640 (0.5); 1.5450 (0.5); 10.5315 (0.4); 1.2448 (3.3); 1.2264 (7.3); 1.2079 (3.2); 1.1062 (5.5); 10.0897 (5.4); 0.0079 (3.1); −0.0002 (780.3); −0.0084 (3.5); −0.1496 (0.4)

I-12 I-12: $^1$H-NMR (400.0 MHz, d$_6$-DMSO): δ=9.2486 (4.0); 8.2755 (4.3); 8.2740 (4.3); 4.2999 (1.5); 4.2852 (2.9); 4.2702 (1.5); 4.0310 (16.0); 3.6868 (1.0); 3.6684 (3.3); 3.6499 (3.4); 3.6315 (1.0); 3.3178 (65.2); 3.0938 (1.4); 3.0781 (2.9); 3.0623 (1.5); 2.6749 (0.7); 2.6705 (1.0); 2.6661 (0.7); 20.5236 (3.4); 23099 (63.1); 2.5059 (1240.2); 2.5014 (162.0); 2.4970 (120.0); 2.3326 (0.8); 2.3281 (1.1); 2.3237 (0.8); 2.0832 (1.0); 2.0765 (1.2); 2.0701 (1.6); 2.0610 (1.3); 2.0404 (0.6); 1.9030 (1.4);

1.8975 (1.2); 1.8881 (1.5); 1.8744 (1.1); 1.2461 (3.4); 1.2277 (7.7); 1.2092 (3.4); 0.0078 (1.6); −0.0003 (44.8); −0.0082 (2.0)

I-13 I-13: ¹H-NMR (400.0 MHz, d₆-DMSO): δ=9.3141 (0.4); 9.2478 (3.7); 8.3456 (0.4); 8.3136 (0.4); 8.2750 (4.1); 8.2730 (4.1); 4.4064 (0.4); 4.3984 (0.4); 4.3919 (0.4); 40.3735 (0.7); 4.3657 (0.6); 4.3591 (0.5); 4.2781 (0.3); 4.2668 (0.5); 40.2496 (0.5); 4.2371 (0.6); 4.2175 (0.3); 4.2057 (0.3); 4.0877 (1.6); 40.0618 (0.3); 4.0304 (16.0); 3.7297 (0.3); 3.7113 (0.3); 3.6880 (0.7); 3.6705 (2.1); 3.6684 (2.1); 3.6498 (2.2); 3.6323 (0.8); 3.3212 (259.2); 3.2842 (0.8); 3.2720 (0.8); 2.6797 (0.4); 2.6752 (1.0); 2.6707 (1.4); 2.6661 (1.0); 2.6615 (0.5); 2.6122 (0.6); 2.5865 (0.7); 2.5677 (0.6); 2.5415 (1.0); 2.5241 (4.8); 2.5193 (6.3); 2.5106 (81.0); 2.5062 (164.8); 2.5016 (216.6); 2.4971 (156.4); 2.4926 (75.8); 2.3374 (0.5); 2.3329 (1.0); 2.3284 (1.4); 2.3238 (1.0); 2.3194 (0.5); 2.1001 (0.7); 2.0737 (1.0); 1.8318 (0.4); 1.8174 (0.5); 1.7985 (0.4); 1.7887 (0.3); 1.7843 (0.4); 1.2455 (3.6); 1.2272 (8.2); 1.2087 (3.5); 1.1372 (4.7); 1.1211 (4.6); 0.0079 (2.1); −0.0002 (68.7); −0.0086 (2.3)

I-14 I-14: ¹H-NMR (601.6 MHz, d₆-DMSO): δ=19.9789 (1.4); 8.9186 (2.0); 8.9154 (2.1); 8.6789 (1.7); 8.3096 (1.0); 3.9575 (16.0); 3.7166 (1.1); 3.7047 (1.0); 3.6829 (1.0); 3.6709 (1.2); 3.3026 (90.0); 2.6119 (2.5); 2.6088 (1.8); 2.5213 (5.7); 2.5181 (7.0); 2.5151 (6.3); 2.5063 (142.3); 23033 (318.3); 2.5002 (458.5); 2.4971 (320.9); 2.4940 (145.4); 2.3875 (1.9); 2.3844 (2.4); 1.2439 (2.9); 1.2316 (7.1); 1.2194 (2.9); 1.1071 (4.7); 1.0960 (4.6); 0.0965 (1.1); 0.0053 (9.9); −0.0002 (370.2); −0.0057 (10.5); −0.1001 (1.0)

I-15 I-15: ¹H-NMR (601.6 MHz, d₆-DMSO): δ=19.9775 (0.5); 9.1201 (2.5); 9.1166 (2.6); 8.9586 (2.2); 8.9551 (2.1); 8.3093 (0.4); 4.4157 (0.5); 4.4071 (0.6); 4.3951 (0.6); 40.3865 (0.6); 3.9955 (16.0); 3.8606 (0.5); 3.8428 (0.7); 3.8225 (0.6); 3.7512 (0.5); 3.7390 (0.7); 3.7276 (1.3); 3.7154 (1.0); 3.7056 (0.4); 3.6936 (1.1); 3.6813 (1.2); 3.6699 (0.7); 3.6577 (0.5); 3.3044 (146.5); 3.2598 (0.5); 2.9689 (0.5); 2.6152 (0.9); 2.6121 (1.2); 2.6091 (0.9); 2.5215 (2.6); 2.5183 (3.2); 2.5153 (2.8); 23065 (67.5); 2.5035 (149.6); 2.5004 (213.6); 2.4973 (150.9); 2.4943 (68.3); 2.3877 (0.9); 2.3846 (1.2); 2.2459 (0.3); 1.9804 (0.4); 1.5775 (0.4); 1.5676 (0.4); 1.5550 (0.4); 1.2476 (3.0); 1.2353 (7.0); 1.2230 (2.9); 1.1081 (4.6); 1.0970 (4.5); 0.0965 (0.5); 0.0052 (5.0); −0.0002 (184.8); −0.0058 (5.6); −0.1001 (0.7)

I-16 I-16: ¹H-NMR (400.2 MHz, d₆-DMSO): δ=8.7157 (5.2); 8.7116 (5.2); 8.3329 (3.6); 8.3112 (7.7); 8.2777 (3.8); 8.2734 (3.6); 8.2559 (1.7); 8.2517 (1.8); 4.4284 (1.4); 40.4160 (1.5); 4.3959 (1.7); 4.3837 (1.6); 3.8732 (1.6); 3.8467 (1.9); 30.8418 (1.8); 3.8147 (1.6); 3.8041 (0.3); 3.7927 (0.9); 3.7850 (0.4); 30.7746 (1.6); 3.7572 (3.8); 3.7392 (4.3); 3.7230 (3.8); 3.7052 (1.5); 30.6874 (0.7); 3.3258 (50.7); 3.3102 (1.0); 3.3026 (1.1); 3.2958 (1.1); 3.2889 (0.9); 3.2637 (1.0); 3.2566 (1.3); 3.2506 (1.3); 3.2433 (1.0); 3.0025 (0.8); 2.9862 (1.0); 2.9752 (0.9); 2.9585 (1.4); 2.9411 (0.8); 2.9296 (0.7); 2.9141 (0.6); 2.6796 (1.3); 2.6751 (1.8); 2.6706 (1.3); 2.6664 (0.7); 2.5285 (5.3); 2.5237 (8.2); 2.5149 (117.7); 2.5107 (241.2); 23062 (318.1); 23017 (226.9); 2.4972 (109.0); 2.3375 (1.4); 2.3329 (1.9); 2.3286 (1.4); 2.2435 (0.9); 2.2326 (0.9); 10.9903 (0.9); 1.9837 (0.9); 1.9738 (0.9); 1.9642 (1.0); 1.9566 (1.1); 10.5965 (0.4); 1.5816 (0.5); 1.5678 (1.0); 1.5541 (1.1); 1.5351 (1.0); 10.5207 (0.8); 1.5070 (0.5); 1.4934 (0.5); 1.3516 (0.5); 1.3331 (1.0); 10.3140 (0.5); 1.2889 (0.5); 1.2760 (7.2); 1.2576 (16.0); 1.2392 (7.3); 1.1031 (11.7); 1.0865 (11.5); 0.0043 (0.7)

I-17 I-17: ¹H-NMR (400.2 MHz, d₆-DMSO): δ=9.2582 (3.6); 8.3157 (0.3); 8.2910 (3.8); 8.2888 (4.0); 4.6285 (0.6); 4.6152 (0.6); 4.5966 (0.8); 4.5831 (0.7); 4.3605 (0.7); 40.3339 (0.9); 4.3115 (1.4); 4.3026 (0.6); 4.0514 (16.0); 3.7604 (0.5); 3.7422 (0.8); 3.7250 (1.4); 3.7065 (1.5); 3.6883 (1.5); 3.6700 (1.4); 3.6526 (0.8); 3.6345 (0.5); 3.4174 (0.4); 3.3682 (0.5); 3.3561 (0.4); 3.3217 (46.7); 3.0949 (0.4); 3.0843 (0.4); 3.0670 (0.6); 3.0386 (0.3); 2.6752 (0.6); 2.6706 (0.9); 2.6660 (0.7); 2.5242 (2.5); 20.5196 (3.8); 2.5108 (52.1); 2.5063 (108.2); 2.5017 (144.2); 2.4971 (104.0); 2.4925 (50.3); 2.3331 (0.7); 2.3285 (0.9); 2.3239 (0.7); 2.3194 (0.4); 2.2738 (0.4); 2.2675 (0.4); 2.2576 (0.4); 2.2499 (0.5); 2.2418 (0.5); 2.0742 (1.6); 1.9927 (0.4); 1.9781 (0.5); 1.9596 (0.4); 1.9452 (0.4); 1.2579 (3.1); 1.2395 (7.4); 1.2210 (3.1); 0.1457 (0.4); 0.0080 (3.6); −0.0002 (117.6); −0.0085 (4.0); −0.0165 (0.3); −0.0172 (0.3); −0.0179 (0.3); −0.1497 (0.5)

I-18 I-18: ¹H-NMR (400.2 MHz, d₆-DMSO): δ=7.4013 (4.4); 4.5894 (0.7); 4.5763 (0.7); 4.5580 (0.9); 4.5445 (0.8); 4.3262 (0.8); 4.2995 (1.0); 4.2685 (0.7); 4.0649 (16.0); 3.6267 (0.7); 3.6108 (8.3); 3.5916 (1.8); 3.5840 (0.6); 3.5730 (1.6); 3.5652 (1.5); 3.5544 (0.6); 33468 (1.6); 3.5295 (0.8); 3.5112 (0.5); 3.4023 (0.5); 3.3242 (140.3); 3.2981 (0.9); 3.2899 (0.9); 3.0840 (1.3); 3.0690 (0.5); 3.0573 (0.5); 3.0405 (0.6); 3.0234 (0.4); 30.0119 (0.4); 2.6752 (0.7); 2.6708 (0.9); 2.6663 (0.7); 2.5239 (4.1); 20.5105 (62.8); 2.5064 (117.4); 2.5019 (147.5); 2.4973 (107.0); 2.4931 (53.4); 2.3332 (0.7); 2.3288 (0.9); 2.3241 (0.7); 2.3197 (0.4); 2.2582 (0.5); 2.2507 (0.5); 2.2408 (0.5); 2.2251 (0.6); 1.9781 (0.5); 1.9639 (0.6); 1.9456 (0.5); 1.9324 (0.4); 1.2182 (3.4); 1.1998 (7.5); 1.1814 (3.3); 0.0078 (3.6); −0.002 (74.6); −0.0084 (3.6); −0.1494 (0.3)

I-19 I-19: ¹H-NMR (400.2 MHz, d₆-DMSO): δ=8.7973 (2.6); 8.7933 (2.6); 8.5973 (2.7); 8.5934 (2.5); 4.6302 (0.7); 4.6171 (0.8); 4.5987 (0.9); 4.5850 (0.9); 4.3648 (0.9); 40.3382 (1.1); 4.3071 (0.8); 3.9614 (16.0); 3.9428 (0.6); 3.7952 (0.6); 3.7773 (0.9); 3.7599 (1.5); 3.7415 (1.4); 3.7168 (1.3); 3.6984 (1.5); 3.6811 (0.9); 3.6629 (0.6); 3.42 43 (0.5); 3.4101 (0.5); 3.3751 (0.8); 3.3626 (0.7); 3.3246 (197.2); 3.1130 (0.4); 3.0972 (0.5); 3.0854 (0.5); 3.0694 (0.7); 3.0522 (0.4); 3.0407 (0.4); 2.6753 (1.0); 20.6710 (1.3); 2.6664 (1.0); 2.5063 (1640.0); 2.5020 (203.0); 2.4976 (1470.5); 2.3332 (1.0); 2.3289 (1.3); 2.3245 (1.0); 2.2749 (0.5); 2.2674 (0.5); 2.2489 (0.6); 2.2414 (0.6); 1.9951 (0.5); 1.9810 (0.6); 1.9618 (0.6); 1.9508 (0.4); 1.2614 (3.4); 1.2430 (7.5); 1.2247 (3.4); 0.1461 (0.4); 0.0078 (4.5); −0.0001 (89.9); −0.0082 (4.6); −0.1495 (0.4)

I-20 I-20: ¹H-NMR (400.2 MHz, d₆-DMSO): δ=8.7248 (4.8); 8.7206 (4.9); 8.3434 (3.7); 8.3217 (7.4); 8.3156 (0.6); 8.2830 (3.6); 8.2785 (3.5); 8.2613 (1.8); 8.2567 (1.8); 40.6396 (1.2); 4.6263 (1.4); 4.6077 (1.7); 4.5943 (1.6); 4.3727 (1.6); 40.3464 (1.9); 4.3410 (1.6); 4.3148 (1.4); 3.8113 (0.9); 3.7932 (1.6); 30.7755 (3.2); 3.7691 (1.0); 3.7570 (3.1); 3.7506 (3.0); 3.7380 (1.1); 30.7322 (3.3); 3.7145 (1.7); 3.6962 (0.9); 3.4165 (0.8); 3.3899 (1.1); 30.3776 (1.2); 3.3687 (1.0); 3.3236 (1880.3); 3.1088 (0.6); 3.0938 (0.9); 3.0830 (0.8); 3.0655 (1.2); 3.0486 (0.6); 3.0371 (0.7); 3.0212 (0.6); 2.6801 (0.4); 2.6756 (0.9); 2.6711 (1.3); 2.6666 (1.0); 2.6622 (0.4); 2.5246 (3.1); 2.5198 (4.8); 2.5111 (75.9); 23067 (157.5); 2.5021 (208.6); 2.4976 (148.1); 2.4931 (69.5); 2.3379 (0.4); 2.3334 (0.9); 2.3289 (1.3); 2.3244 (1.0); 2.3199 (0.4); 2.2632 (0.8); 2.2559 (0.8); 2.2460 (0.8); 2.2371 (1.0); 2.2294 (1.0); 2.0744 (1.0); 2.0102 (0.4); 1.9959

(0.5); 1.9822 (0.9); 1.9681 (1.0); 1.9497 (0.9); 1.9353 (0.8); 1.9217 (0.4); 1.9076 (0.3); 1.2771 (7.0); 1.2587 (16.0); 1.2403 (6.9); 0.1459 (0.9); 0.0080 (6.8); −0.0002 (211.3); −0.0086 (6.4); −0.1495 (0.9)

Use Examples

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples show an efficacy of 100% at an application rate of 5 µg/cm$^2$ (=500 g/ha): I-05.

*Rhipicephalus sanguineus*—In Vitro Contact Tests with Adult Brown Doer Ticks

For the coating of the test tubes, 9 mg of active ingredient are first dissolved in 1 ml of acetone p.a. and then diluted to the desired concentration with acetone p.a. 250 µl of the solution are distributed homogeneously on the inner walls and base of a 25 ml test tube by turning and rocking on an orbital shaker (rocking rotation at 30 rpm for 2 h). With 900 ppm active ingredient solution and internal surface 44.7 cm$^2$, given homogeneous distribution, an area-based dose of 5 µg/cm$^2$ is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the floor of the tube and incubated on a hotplate at 45-50° C. for not more than 5 min. Ticks which remain motionless on the floor or move in such an uncoordinated manner that they are unable to deliberately avoid the heat by climbing upwards are considered to be dead or moribund.

A substance shows good efficacy against *Rhipicephalus sanguineus* if at least 80% efficacy was achieved in this test at an application rate of 5 µg/cm$^2$. 100% efficacy means that all the ticks were dead or moribund. 0% efficacy means that none of the ticks had been harmed.

In this test, for example, the following compounds from the preparation examples show an efficacy of 100% at an application rate of 5 µg/cm$^2$ (=500 g/ha): I-05.

*Boophilus microplus*—Injection Test
Solvent: dimethyl sulfoxide

To produce a suitable active ingredient formulation, 10 mg of active ingredient are mixed with 0.5 ml of solvent and the concentrate is diluted to the desired concentration with solvent.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 µg/animal: I-05, I-13.

*Ctenocephalides felis*—Oral Test
Solvent: dimethyl sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-11, I-13.

In this test, for example, the following compounds from the preparation examples show an efficacy of 95% at an application rate of 100 ppm: I-05.

In this test, for example, the following compounds from the preparation examples show an efficacy of 90% at an application rate of 100 ppm: I-02, I-15.

*Lucius cuprina* Test
Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active ingredient formulation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-02.

*Musca domestica* Test
Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 80% at an application rate of 100 ppm: I-02, I-05.

*Diabrotica balteata*—Spray Test

| Solvent: | 78 parts by weight of acetone |
| | 1.5 parts by weight of dimethylformamide |
| Emulsifier: | alkylaryl polyglycol ether |

To produce an appropriate active ingredient formulation, 1 part by weight of active ingredient is dissolved with the given parts by weight of solvent and made up with water containing an emulsifier concentration of 1000 ppm until the desired concentration is attained. Further test concentrations are produced by diluting with emulsifier-containing water.

Pre-swollen wheat grains (*Triticum aestivum*) are incubated in a multiwell plate filled with agar and a little water for one day (5 seed grains per cavity). The germinated wheat grains are sprayed with an active ingredient formulation of the desired concentration. Subselog Puently, each cavity is infected with 10-20 *Diabrotica balteata* beetle larvae.

After 7 days, efficacy in % is determined. 100% means that all wheat plants have grown as in the untreated, uninfected control; 0% means that no wheat plant has grown.

In this test, for example, the following compounds from the preparation examples show efficacy of 100% at an application rate of 160 µg/cavity: I-17, I-18, I-19.

*Myzus persicae*—Oral Test

| Solvent: | 100 parts by weight of acetone |

To produce a suitable active ingredient formulation, 1 part by weight of active ingredient is dissolved with the stated parts by weight of solvent and made up to the desired concentration with water.

50 µl of the active ingredient preparation are transferred into microtitre plates and made up to a final volume of 200 µl with 150 µl of IPL41 insect medium (33%+15% sugar). Subselog Puently, the plates are sealed with parafilm, which a mixed population of green peach aphids (*Myzus persicae*) within a second microtitre plate is able to puncture and imbibe the solution.

After 5 days, the efficacy in % is determined. 100% means that all the aphids have been killed; 0% means that no aphids have been killed.

In this test, for example, the following compounds from the preparation examples show efficacy of 100% at an application rate of 4 ppm: I-01, I-02, I-03, I-04, I-05, I-07, I-08, I-10, I-11, I-12, I-13, I-14, I 17, I-18, I-19.

In this test, for example, the following compounds from the preparation examples show an efficacy of 90% at an application rate of 4 ppm: I-09, I-15, I-16.

*Myzus persicae*—Spray Test

| Solvent: | 78 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: I-04, I-05, I-14.

In this test, for example, the following compounds from the preparation examples show an efficacy of 90% at an application rate of 100 g/ha: I-02, I-03, I-06, I-09, I-10, I-11, I-12, I-13, I-15, I-18.

*Phaedon cochleariae*—Spray Test

| Solvent: | 78.0 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: I-01, I-03, I-12.

*Spodoptera frugiperda*—Spray Test

| Solvent: | 78.0 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: I-01, I-08, I-13, I-15, I-17, I-19.

In this test, for example, the following compounds from the preparation examples show an efficacy of 83% at an application rate of 100 g/ha: I-11.

*Tetranychus urticae*—Spray Test, OP-Resistant

| Solvent: | 78.0 parts by weight of acetone |
| --- | --- |
|  | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 100 g/ha: I-04, I-13.

In this test, for example, the following compounds from the preparation examples shows an efficacy of 90% at an application rate of 100 g/ha: I-10.

The invention claimed is:

1. Compound of the formula (I)

$$(O)_n=S^{R^1} \quad Q \underset{N-N}{\overset{A_d}{\underset{A_a}{\bigvee}}} \overset{A_c}{\underset{A_b}{\bigvee}}$$
(I)

in which

Aa is —C(R$^8$)(R$^9$)—,
Ab is —C(R$^{10}$)(R$^{11}$)—,
Ac is —C(R$^{12}$)(R$^{13}$)—,
Ad is —C(R$^{14}$)(R$^{15}$)—,
R$^1$ is ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, amino, ($C_1$-$C_6$)-alkylamino, di-($C_1$-$C_6$)-alkyl-amino, ($C_3$-$C_8$)-cycloalkylamino, ($C_1$-$C_6$)-alkylcarbonylamino, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulfinyl-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-alkyl, ($C_1$-$C_6$)-haloalkylsulfonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulfinyl-($C_1$-$C_6$)-alkyl, ($C_1$-$C_6$)-alkoxy-($C_1$-$C_6$)-alkylsulfonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkylsulfonylamino, aminosulfonyl-($C_1$-$C_6$)-alkyl, ($C_1$-$C_6$)-alkylaminosulfonyl-($C_1$-$C_6$)-alkyl, di-($C_1$-$C_6$)-alkylaminosulfonyl-($C_1$-$C_6$)-alkyl, R$^8$, R$^9$, R$^{10}$, R$^{11}$, R$^{12}$, R$^{13}$, R$^{14}$, R$^{15}$ are independently hydrogen, cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, cyano-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$1-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), are in each case optionally singly or multiply, identically or differently substituted aryl or hetaryl, where (in the case of hetaryl) at least one carbonyl group may optionally be present and/or where possible substituents in each case are as follows: cyano, carboxyl, halogen, nitro, acetyl, hydroxyl, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkylaminocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, Q is a partly saturated or saturated heterocyclic or heteroaromatic 8-, 9-, 10-, 11- or 12-membered fused bicyclic or tricyclic ring system where at least one carbonyl group may optionally be present and/or where the ring system is optionally mono- or polysubstituted identically or differently, and where the substituents may independently be selected from cyano, halogen, nitro, acetyl, hydroxyl, amino, SCN, tri-$(C_1-C_6)$-alkylsilyl, $(C_8-C_8)$-cycloalkyl, cyano-$(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_8-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_4)$-alkyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-haloalkoxy-$(C_1-C_6)$-alkyl, $(C_2-C_6)$-alkenyloxy-$(C_1-C_6)$-alkyl, $(C_2-C_6)$-haloalkenyloxy-$(C_1-C_6)$-alkyl, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylcarbonyl-$(C_1-C_6)$-alkyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkyl-aminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkyl-aminosulfonyl, $(C_1-C_6)$-alkylsulfoximino, aminothiocarbonyl, $(C_1-C_6)$-alkylaminothiocarbonyl, di-$(C_1-C_6)$-alkyl-aminothiocarbonyl, $(C_3-C_8)$-cycloalkylamino, NHCO—$(C_1-C_6)$-alkyl ($(C_1-C_6)$-alkylcarbonylamino), or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $NO_2$, $C_1-C_4$-alkoxy, $C_1-C_4$-haloalkoxy, n is 0, 1 or 2.

2. Compound of formula (I) according to claim 1 in which

Aa is —C(R$^8$)(R$^9$)—,
Ab is —C(R$^{10}$)(R$^{11}$)—,
Ac is —C(R$^{12}$)(R$^{13}$)—,
Ad is —C(R$^{14}$)(R$^{15}$)—,

R$^1$ is $(C_1-C_4)$alkyl, $(C_1-C_4)$hydroxyalkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyloxy-$(C_1-C_4)$alkyl, $(C_2-C_4)$haloalkynyl, $(C_2-C_4)$cyanoalkynyl, $(C_3-C_6)$cycloalkyl, $(C_3-C_6)$cycloalkyl($C_3-C_6$)cycloalkyl, $(C_1-C_4)$alkyl-$(C_3-C_6)$cycloalkyl, halo-$(C_3-C_6)$cycloalkyl, $(C_1-C_4)$alkylamino, di-$(C_1-C_4)$alkyl-amino, $(C_3-C_6)$cycloalkylamino, $(C_1-C_4)$alkylcarbonyl-amino, $(C_1-C_4)$alkylthio-$(C_1-C_4)$alkyl, $(C_1-C_4)$haloalkylthio-$(C_1-C_4)$alkyl, $(C_1-C_4)$alkylsulfinyl-$(C_1-C_4)$alkyl, $(C_1-C_4)$haloalkylsulfinyl-$(C_1-C_4)$alkyl, $(C_1-C_4)$alkylsulfonyl-$(C_1-C_4)$alkyl, $(C_1-C_4)$alkylcarbonyl-$(C_1-C_4)$alkyl, $(C_1-C_4)$haloalkylcarbonyl-$(C_1-C_4)$alkyl, $(C_1-C_4)$alkylsulfonylamino, R$^8$, R$^9$, R$^{10}$, R$^{11}$, R$^{12}$, R$^{13}$, R$^{14}$, R$^{15}$ are independently hydrogen, cyano, halogen, nitro, acetyl, hydroxyl, amino, SCN, tri-$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo-$(C_3-C_6)$cycloalkyl, cyano-$(C_3-C_6)$-cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$haloalkyl-$(C_1-C_4)$alkoxyimino, $(C_1-C_4)$alkylthio, $(C_1-C_4)$haloalkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkylsulfonyl-$(C_1-C_4)$alkyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylamino, di-$(C_1-C_4)$alkylamino, aminosulfonyl, $(C_1-C_4)$alkylaminosulfonyl, di-$(C_1-C_4)$alkylaminosulfonyl, aminothiocarbonyl, NHCO—$(C_1-C_4)$alkyl (($C_1-C_4$) alkylcarbonylamino), and also are phenyl or hetaryl, each of which is optionally mono- or disubstituted identically or differently, where (in the case of hetaryl) at least one carbonyl group may optionally be present and/or where possible substituents are in each case as follows: cyano, halogen, nitro, acetyl, amino, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino), Q is a heteroaromatic 8-, 9-, 10-, 11- or 12-membered fused bicyclic or tricyclic ring system, where at least one carbonyl group may optionally be present and/or where the ring system is optionally mono- or polysubstituted identically or differently and where the substituents may independently be selected from cyano, halogen, nitro, acetyl, hydroxyl, amino, SCN, tri-($C_1$-$C_6$)-alkylsilyl, ($C_3$-$C_8$)-cycloalkyl, cyano-($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_4$)-alkyl, ($C_2$-$C_6$)-haloalkynyl, ($C_1$-$C_6$)-alkoxy, ($C_1$-$C_6$)-haloalkoxy, ($C_1$-$C_6$)-haloalkoxy-($C_1$-$C_6$)-alkyl, ($C_2$-$C_6$)-alkenyloxy-($C_1$-$C_6$)-alkyl, ($C_2$-$C_6$)-haloalkenyloxy-($C_1$-$C_6$)-alkyl, ($C_1$-$C_6$)-cyanoalkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylcarbonyl-($C_1$-$C_6$)-alkyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), or where the substituents may independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n is 0, 1 or 2.

3. Compound of formula (I) according to claim 1 in which
Aa is —C($R^8$)($R^9$)—,
Ab is —C($R^{10}$)($R^{11}$)—,
Ac is —C($R^{12}$)($R^{13}$)—,
Ad is —C($R^{14}$)($R^{15}$)—,
$R^1$ is ($C_1$-$C_4$)-alkyl, ($C_1$-$C_4$)-hydroxyalkyl, ($C_1$-$C_4$)-haloalkyl, ($C_2$-$C_4$)-alkenyl, ($C_2$-$C_4$)-haloalkenyl, ($C_2$-$C_4$)-alkynyl, ($C_2$-$C_4$)-haloalkynyl, ($C_3$-$C_6$)-cycloalkyl, ($C_1$-$C_4$)-alkylthio-($C_1$-$C_4$)-alkyl, ($C_1$-$C_4$)-alkylsulfinyl-($C_1$-$C_4$)-alkyl or ($C_1$-$C_4$)-alkylsulfonyl-($C_1$-$C_4$)-alkyl,
$R^8$, $R^9$, $R^{10}$, $R^{11}$, $R^{12}$, $R^{13}$, $R^{14}$, $R^{15}$ are independently hydrogen, cyano, halogen, nitro, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano-($C_3$-$C_8$)-cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkyl-aminosulfonyl, NHCO—($C_1$-$C_4$)alkyl (($C_1$-$C_4$)alkylcarbonylamino),
and also are phenyl or hetaryl, each of which is optionally mono- or disubstituted identically or differently, where (in the case of hetaryl) at least one carbonyl group may optionally be present and/or where possible substituents are in each case as follows: cyano, halogen, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino),
Q is a heteroaromatic 9-membered or 12-membered fused bicyclic or tricyclic ring system from the group of Q1 to Q21,

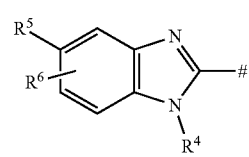

Q1

-continued

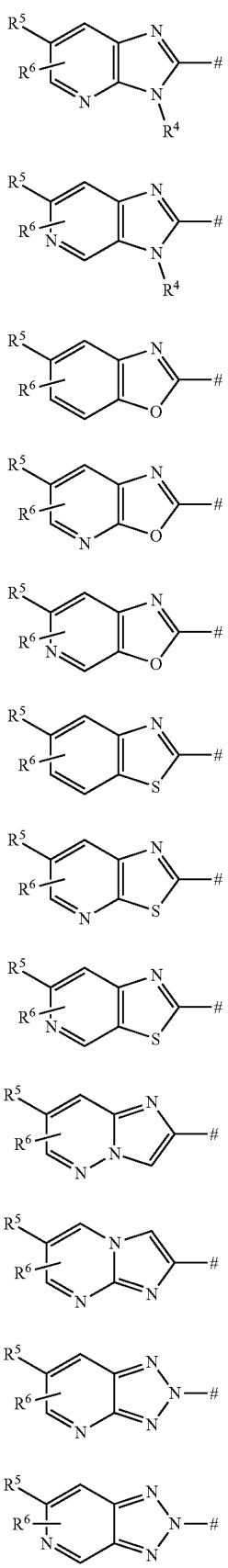

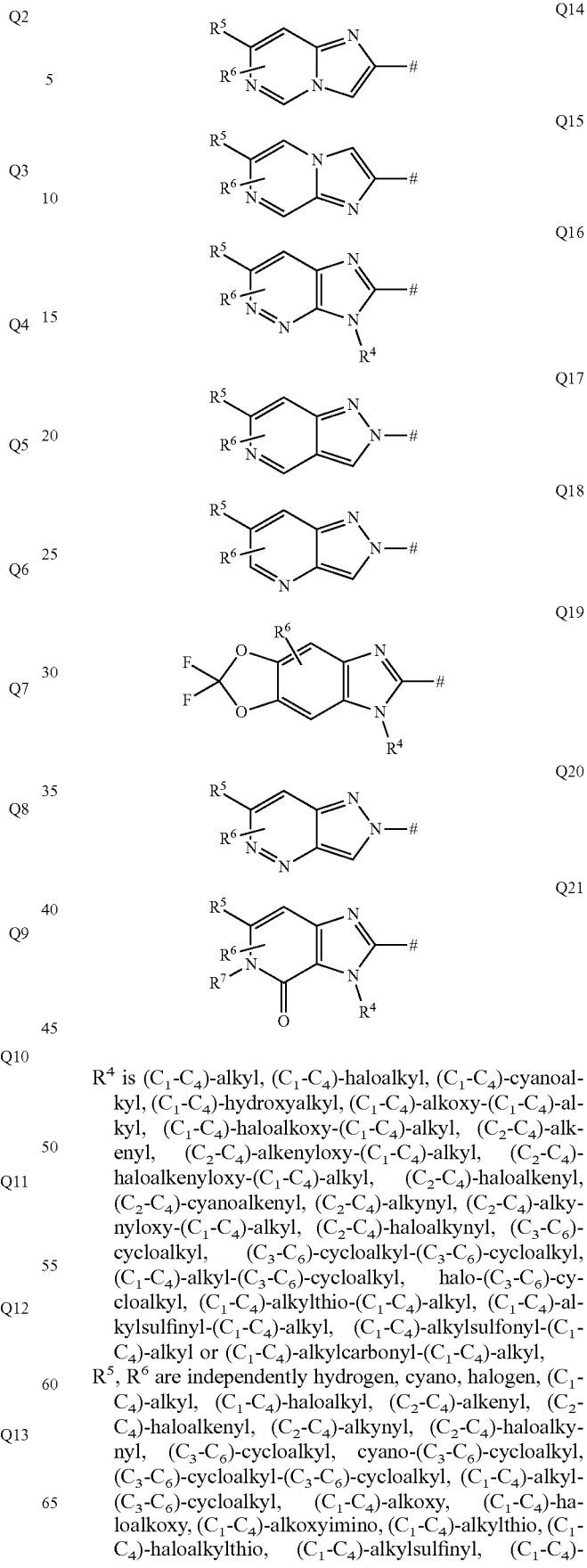

R⁴ is (C₁-C₄)-alkyl, (C₁-C₄)-haloalkyl, (C₁-C₄)-cyanoalkyl, (C₁-C₄)-hydroxyalkyl, (C₁-C₄)-alkoxy-(C₁-C₄)-alkyl, (C₁-C₄)-haloalkoxy-(C₁-C₄)-alkyl, (C₂-C₄)-alkenyl, (C₂-C₄)-alkenyloxy-(C₁-C₄)-alkyl, (C₂-C₄)-haloalkenyloxy-(C₁-C₄)-alkyl, (C₂-C₄)-haloalkenyl, (C₂-C₄)-cyanoalkenyl, (C₂-C₄)-alkynyl, (C₂-C₄)-alkynyloxy-(C₁-C₄)-alkyl, (C₂-C₄)-haloalkynyl, (C₃-C₆)-cycloalkyl, (C₃-C₆)-cycloalkyl-(C₃-C₆)-cycloalkyl, (C₁-C₄)-alkyl-(C₃-C₆)-cycloalkyl, halo-(C₃-C₆)-cycloalkyl, (C₁-C₄)-alkylthio-(C₁-C₄)-alkyl, (C₁-C₄)-alkylsulfinyl-(C₁-C₄)-alkyl, (C₁-C₄)-alkylsulfonyl-(C₁-C₄)-alkyl or (C₁-C₄)-alkylcarbonyl-(C₁-C₄)-alkyl, R⁵, R⁶ are independently hydrogen, cyano, halogen, (C₁-C₄)-alkyl, (C₁-C₄)-haloalkyl, (C₂-C₄)-alkenyl, (C₂-C₄)-haloalkenyl, (C₂-C₄)-alkynyl, (C₂-C₄)-haloalkynyl, (C₃-C₆)-cycloalkyl, cyano-(C₃-C₆)-cycloalkyl, (C₃-C₆)-cycloalkyl-(C₃-C₆)-cycloalkyl, (C₁-C₄)-alkyl-(C₃-C₆)-cycloalkyl, (C₁-C₄)-alkoxy, (C₁-C₄)-haloalkoxy, (C₁-C₄)-alkoxyimino, (C₁-C₄)-alkylthio, (C₁-C₄)-haloalkylthio, (C₁-C₄)-alkylsulfinyl, (C₁-C₄)- haloalkylsulfinyl, $(C_1-C_4)$-alkylsulfonyl, $(C_1-C_4)$-haloalkylsulfonyl, $(C_1-C_4)$-alkylsulfonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulfonylamino, $(C_1-C_4)$-alkylamino, di-$(C_1-C_4)$-alkylamino, aminosulfonyl, $(C_1-C_4)$-alkylaminosulfonyl or di-$(C_1-C_4)$-alkylaminosulfonyl, $R^7$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulfinyl-$(C_1-C_4)$alkyl or $(C_1-C_4)$alkylsulfonyl-$(C_1-C_4)$alkyl, n is 0, 1 or 2.

4. Compound of formula (I) according to claim 1 in which
Aa is —C($R^8$)($R^9$)—,
Ab is —C($R^{10}$)($R^{11}$)—,
Ac is —C($R^{12}$)($R^{13}$)—,
Ad is —C($R^{14}$)($R^{15}$)—,
$R^1$ is methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl,
$R^8, R^9, R^{10}, R^{11}, R^{12}, R^{13}, R^{14}, R^{15}$ are independently hydrogen, cyano, halogen, $(C_1-C_4)$alkyl, $(C_3-C_6)$-cycloalkyl, cyano-$(C_3-C_6)$-cycloalkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl or NHCO—$(C_1-C_4)$alkyl(($C_1-C_4$)alkylcarbonylamino),
Q is a heteroaromatic 9-membered or 12-membered fused bicyclic or tricyclic ring system from the group of Q2, Q3, Q4, Q10, Q11, Q14, Q15, Q16, Q19, Q20 or Q21,

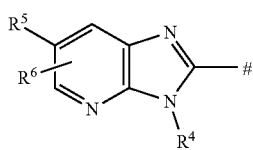
Q2

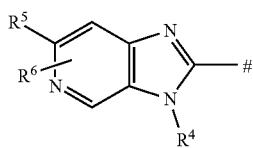
Q3

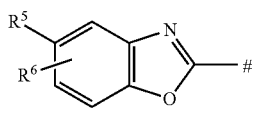
Q4

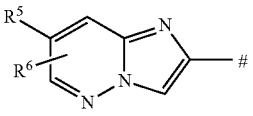
Q10

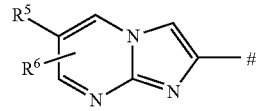
Q11

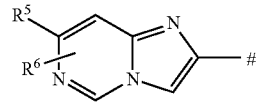
Q14

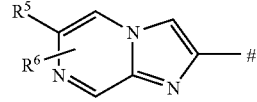
Q15

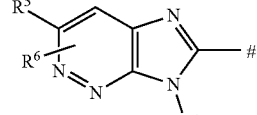
Q16

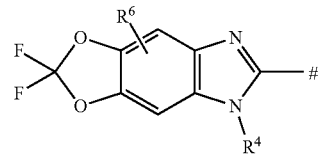
Q19

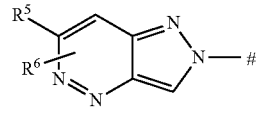
Q20

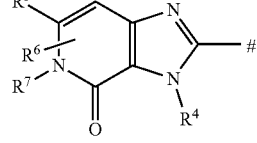
Q21

$R^4$ is $(C_1-C_4)$alkyl or $(C_1-C_4)$alkoxy-$(C_1-C_4)$-alkyl, $R^5$ is hydrogen, cyano, halogen, $(C_1-C_4)$alkyl, $(C_1-C_4)$haloalkyl, $(C_3-C_6)$cycloalkyl, cyano-$(C_3-C_6)$-cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylcarbonyl, $(C_1-C_4)$haloalkylcarbonyl, $(C_1-C_4)$alkylaminocarbonyl, di-$(C_1-C_4)$alkylaminocarbonyl, $(C_1-C_4)$alkylsulfonylamino, $(C_1-C_4)$alkylaminosulfonyl or di-$(C_1-C_4)$alkylaminosulfonyl, $R^6$ is hydrogen or methyl, $R^7$ is hydrogen, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$haloalkenyl, $(C_2-C_4)$-cyanoalkenyl, $(C_2-C_4)$alkynyl, $(C_2-C_4)$-haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulfinyl-$(C_1-C_4)$alkyl or $(C_1-C_4)$alkylsulfonyl-$(C_1-C_4)$alkyl, n is 0, 1 or 2.

5. Compound of formula (I) according to claim 1 in which
Aa is —C($R^8$)($R^9$)—,
Ab is —C($R^{10}$)($R^{11}$)—,
Ac is —C($R^{12}$)($R^{13}$)—,
Ad is —C($R^{14}$)($R^{15}$)—,
$R^1$ is methyl, ethyl, n-propyl, i-propyl or cyclopropyl,
$R^8$, $R^9$, $R^{10}$, $R^{11}$, $R^{12}$, $R^{13}$, $R^{14}$, $R^{15}$ are independently hydrogen, cyano, cyclopropyl, cyclobutyl, cyanocyclopropyl, fluorine, chlorine, bromine, methyl, ethyl, trifluoromethyl, difluoromethyl, trifluoroethyl, methoxy or ethoxy,
Q is a heteroaromatic 9-membered fused bicyclic ring system from the group of Q2, Q3, Q4, Q10, Q14, Q16 or Q21,

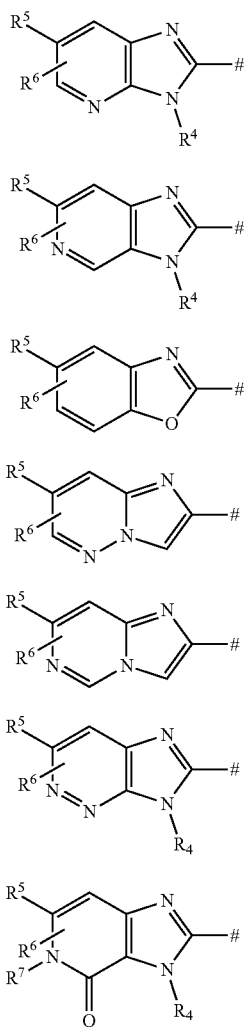

$R^4$ is methyl, ethyl, isopropyl, methoxymethyl or methoxyethyl,
$R^5$ is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulfinyl, trifluoromethylsulfonyl or cyanocyclopropyl, $R^6$ is hydrogen,
$R^7$ is methyl, ethyl, i-propyl, cyclopropyl, methoxymethyl or methoxyethyl,
n is 0, 1 or 2.

6. Compound of formula (I) according to claim 1 in which
Aa is —C($R^8$)($R^9$)—,
Ab is —C($R^{10}$)($R^{11}$)—,
Ac is —C($R^{12}$)($R^{13}$)—,
Ad is —C($R^{14}$)($R^{15}$)—,
$R^1$ is ethyl,
$R^8$ is hydrogen,
$R^9$ is hydrogen,
$R^{10}$ is hydrogen, methyl or trifluoromethyl,
$R^{11}$ is hydrogen,
$R^{12}$ is hydrogen, methyl or trifluoromethyl,
$R^{13}$ is hydrogen,
$R^{14}$ is hydrogen,
$R^{15}$ is hydrogen,
Q is a heteroaromatic 9-membered fused bicyclic ring system from the group of Q2, Q3, Q4 or Q21,
$R^4$ is methyl,
$R^5$ is trifluoromethyl, pentafluoroethyl, trifluoromethoxy, trifluoromethylthio, trifluoromethylsulfinyl or trifluoromethylsulfonyl,
$R^5$ is hydrogen,
$R^7$ is methyl,
n is 2.

7. Compound of formula (I) according to claim 1, in which the compounds have the following structures:

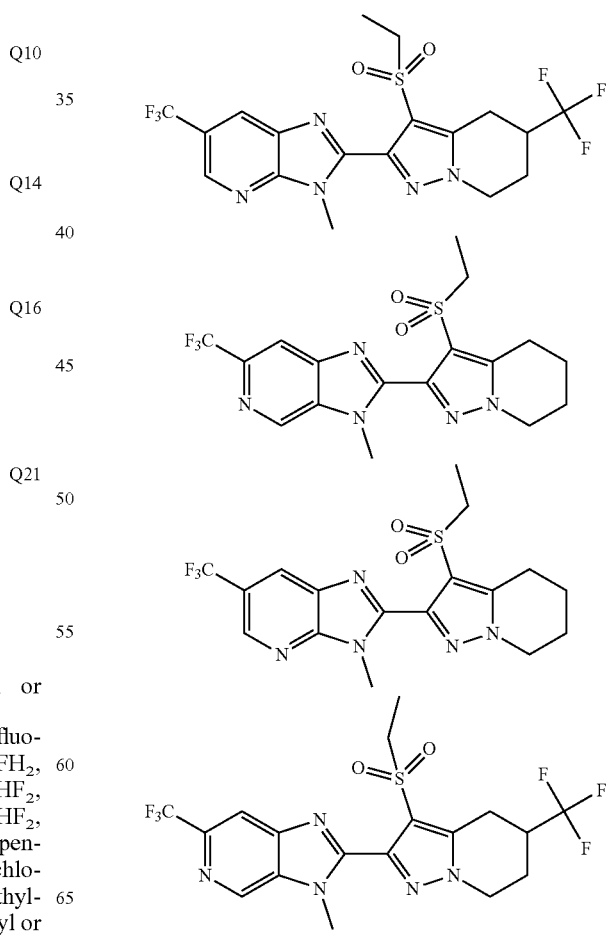

-continued
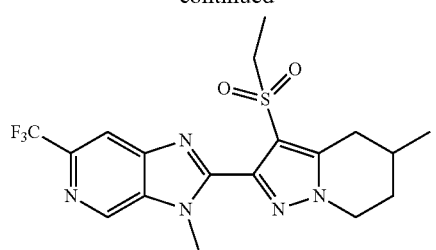
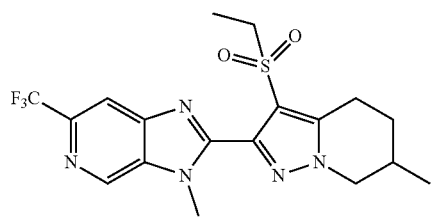
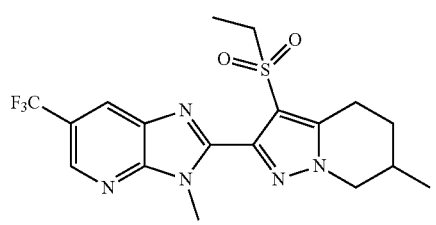
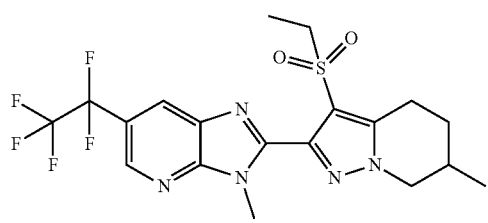
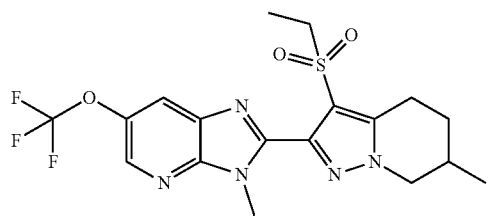
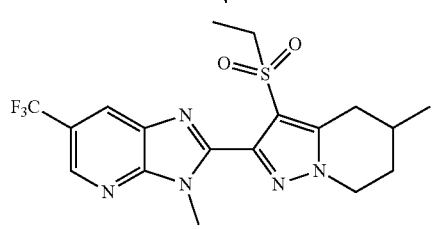
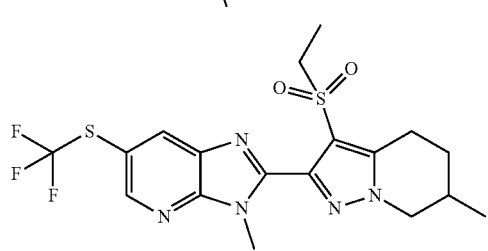
-continued
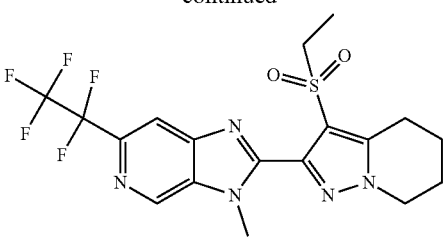
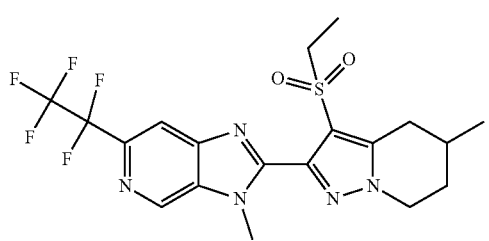
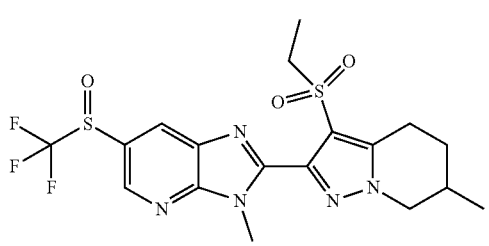
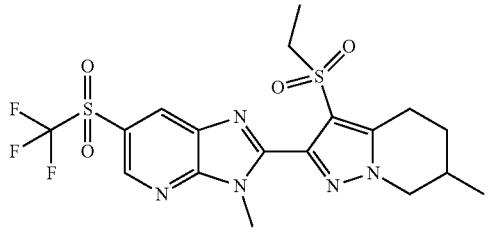
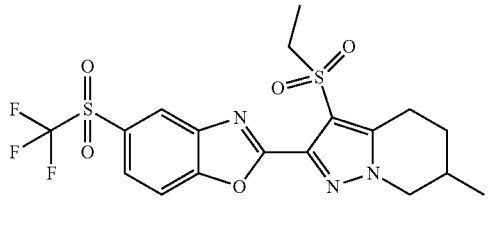
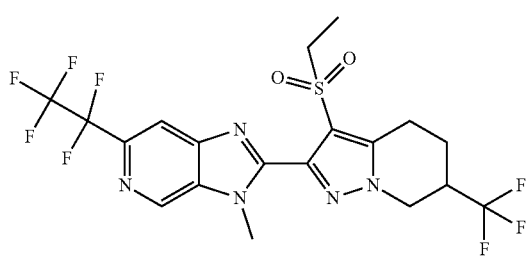

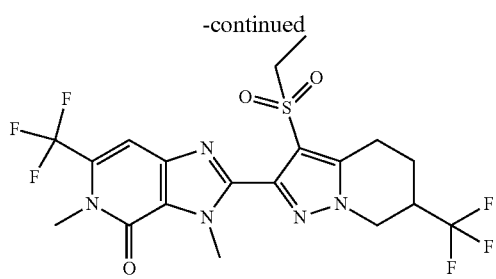

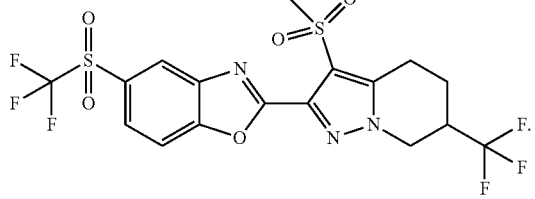

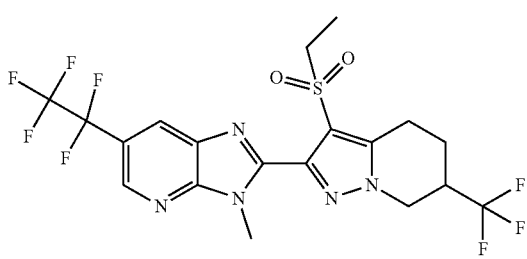

8. Agrochemical formulation comprising one or more compounds of formula (I) according to claim 1 and one or more extenders and/or surfactants.

9. Agrochemical formulation according to claim 8, additionally comprising a further agrochemically active ingredient.

10. Method for controlling animal pests, comprising allowing a compound of formula (I) according to claim 1 or an agrochemical formulation thereof to act on the animal pests and/or a habitat thereof.

11. A product comprising one or more compounds of formula (I) according to claim 1 or an agrochemical formulation thereof for controlling one or more animal pests.

\* \* \* \* \*